United States Patent
Clemens et al.

(10) Patent No.: US 12,220,404 B2
(45) Date of Patent: *Feb. 11, 2025

(54) TREATMENT AND MANAGEMENT OF AUGMENTATION IN RESTLESS LEGS SYNDROME

(71) Applicant: East Carolina University, Greenville, NC (US)

(72) Inventors: Stefan Clemens, Greenville, NC (US); Perrine Lallemand, Frederick, MD (US)

(73) Assignee: East Carolina University, Greenville, NC (US)

( * ) Notice: Subject to any disclaimer, the term of this patent is extended or adjusted under 35 U.S.C. 154(b) by 598 days.

This patent is subject to a terminal disclaimer.

(21) Appl. No.: 16/932,352

(22) Filed: Jul. 17, 2020

(65) Prior Publication Data

US 2021/0169859 A1 Jun. 10, 2021

Related U.S. Application Data

(63) Continuation of application No. 15/753,149, filed as application No. PCT/US2016/047591 on Aug. 18, 2016, now Pat. No. 10,751,327.

(60) Provisional application No. 62/207,225, filed on Aug. 19, 2015.

(51) Int. Cl.
| | | |
|---|---|---|
| *A01N 37/00* | (2006.01) | |
| *A01N 25/00* | (2006.01) | |
| *A01N 37/12* | (2006.01) | |
| *A01N 37/44* | (2006.01) | |
| *A61K 31/215* | (2006.01) | |
| *A61K 31/24* | (2006.01) | |
| *A61K 31/381* | (2006.01) | |
| *A61K 31/40* | (2006.01) | |
| *A61K 31/428* | (2006.01) | |
| *A61K 31/48* | (2006.01) | |
| *A61K 31/485* | (2006.01) | |
| *A61K 31/5383* | (2006.01) | |
| *A61K 31/55* | (2006.01) | |
| *A61K 45/06* | (2006.01) | |
| *A61P 43/00* | (2006.01) | |
| *A61K 9/00* | (2006.01) | |

(52) U.S. Cl.
CPC .......... *A61K 31/428* (2013.01); *A61K 31/381* (2013.01); *A61K 31/40* (2013.01); *A61K 31/48* (2013.01); *A61K 31/485* (2013.01); *A61K 31/5383* (2013.01); *A61K 31/55* (2013.01); *A61K 45/06* (2013.01); *A61P 43/00* (2018.01); *A61K 9/0019* (2013.01); *A61K 2300/00* (2013.01)

(58) Field of Classification Search
None
See application file for complete search history.

(56) References Cited

U.S. PATENT DOCUMENTS

| | | |
|---|---|---|
| 2009/0042956 A1 | 2/2009 | Bozik et al. |
| 2009/0156581 A1 | 6/2009 | Dillon et al. |
| 2010/0168085 A1 | 7/2010 | Eisenbach-Schwartz et al. |
| 2011/0262442 A1 | 10/2011 | Hamilton et al. |

FOREIGN PATENT DOCUMENTS

| | | |
|---|---|---|
| WO | 2002100350 A2 | 12/2002 |
| WO | 2014012063 A1 | 1/2014 |

OTHER PUBLICATIONS

Paulus et al. (Less is more: pathophysiology of dopaminergic-therapy-related augmentation in restless legs syndrome. The Lancet Neurologyvol. 5, Issue 10, Oct. 2006, pp. 878-886).*
Ferini-Strambi (Restless legs syndrome augmentation and pramipexole treatment, Sleep Medicine, vol. 3, Supplement, 2002, pp. S23-S25, ISSN 1389-9457).*
"Bekhit, M.H. "Opioid-induced hyperalgesia and tolerance" American Journal of Therapeutics, 17(5):498-510 (2010) (Abstract only)".
"ClinicalTrials.gov "Ecopipam Treatment of Tourette's Syndrome in Subjects 7-17 Years" https://clinicaltrials.gov/ct2/show/study/NCT02102698#wrapper (9 pages) (2014)".
"Davies S. "Rotigotine for restless legs syndrome" Drugs Today (Barc), 45(9):663-668 (2009) (Abstract only)".
"Earley, C.J. "Latest guidelines and advances for treatment of restless legs syndrome" The Journal of Clinical Psychiatry, 75(4):e08 (2014) (Abstract only)".
"Erman, M.K. "Selected sleep disorders: restless legs syndrome and periodic limb movement disorder, sleep apnea syndrome, and narcolepsy" The Psychiatric Clinics of North America, 29(4):947-967; abstract viii-ix (2006) (Abstract only)".
"Extended European Search Report corresponding to European Application No. 16837850.3 dated May 22, 2019".
"Hubble, J.P. "Pre-clinical studies of pramipexole: clinical relevance" European Journal of Neurology, 7(S1):15-20 (2000) (Abstract only)".
"International Search Report and the Written Opinion of the International Searching Authority corresponding to International Patent Application No. PCT/US2016/047591 (14 pages) (mailed Nov. 30, 2016)".
"Rascol, O. "Dopamine agonists: what is the place of the newer compounds in the treatment of Parkinson's disease?" Journal of Neural Transmission Supplementum, 55:33-45 (1999) (Abstract only)".
"Wei, L. "Immunological aspect of cardiac remodeling: T lymphocyte subsets in inflammation-mediated cardiac fibrosis" Experimental and Molecular Pathology, 90(1):74-78 (2011) (Abstract only)".

(Continued)

*Primary Examiner* — Layla Soroush
(74) *Attorney, Agent, or Firm* — Myers Bigel, P.A.

(57) ABSTRACT

The present invention provides methods of treating Restless Legs Syndrome (RLS) including administering to a subject an effective amount of a dopamine $D_1$ receptor antagonist. Compositions and kits useful for treating RLS are also provided.

12 Claims, 9 Drawing Sheets

(56) References Cited

OTHER PUBLICATIONS

"Winkelmann, J. "Genetics of restless legs syndrome" Current Neurology and Neuroscience Reports, 8(3):211-216 (2008) (Abstract only)".

Allen, et al., ""A randomized, double-blind, 6-week, dose-ranging study of pregabalin in patients with restless legs syndrome" Sleep Medicine, 11(6):512-519 (2010) (Abstract only)".

Allen, et al., ""Augmentation of the restless legs syndrome with carbidopa/levodopa" Sleep, 19(3):205-213 (1996) (Abstract only)".

Allen, et al., ""Restless legs syndrome/Willis-Ekbom disease diagnostic criteria: updated International Restless Legs Syndrome Study Group (IRLSSG) consensus criteria—history, rationale, description, and significance" Sleep Medicine, 15(8):860-873 (2014) (Abstract only)".

Allouche, et al., ""Opioid receptor desensitization: mechanisms and its link to tolerance" Frontiers in Pharmacology 5(280):1-20 (2014)".

Baier, et al., ""Circadian variation in restless legs syndrome" Sleep Medicine, 8(6):645-650 (2007) (Abstract only)".

Barriere, et al., ""The restless legs syndrome" Progress in Neurobiology, 77(3):139-165 (2005) (Abstract only)".

Bayard, et al., ""Decision-making, Reward-Seeking Behaviors and Dopamine Agonist Therapy in Restless Legs Syndrome" Sleep, 36(10):1501-1507 (2013)".

Breese, et al., ""Peripheral inflammation selectively increases TRPV1 function in IB4-positive sensory neurons from adult mouse" Pain, 115(1-2):37-49 (2005) (Abstract only)".

Brewer, et al., ""Dopamine D3 receptor dysfunction prevents anti-nociceptive effects of morphine in the spinal cord" Frontiers in Neural Circuits, 8:62-01-62-10 (2014)".

Bubenikova-Valesova, et al., ""The effect of a full agonist/ antagonist of the D1 receptor on locomotor activity, sensorimotor gating and cognitive function in dizocilpine-treated rats" International Journal of Neuropsychopharmacology, 12(7):873-883 (2009)".

Chahine, et al., ""Restless legs syndrome: a review" CNS Spectrums, 11(7):511-520 (2006) (Abstract only)".

Clemens, et al., ""Conversion of the Modulatory Actions of Dopamine on Spinal Reflexes from Depression to Facilitation in D3 Receptor Knock-Out Mice" The Journal of Neuroscience, 24(50):11337-11345 (2004)".

Clemens, et al., ""Opposing modulatory effects of D1- and D2-like receptor activation on a spinal central pattern generator" Journal of Neurophysiology, 107(8):2250-2259 (2012)".

Clemens, et al., ""Restless legs syndrome: revisiting the dopamine hypothesis from the spinal cord perspective" Neurology, 67(1):125-130 (2006)".

Connor, et al., ""Postmortem and imaging based analyses reveal CNS decreased myelination in restless legs syndrome" Sleep Medicine, 12(6):614-619 (2011)".

Cote, et al., ""In vitro and in vivo characterization of the agonist-dependent D3 dopamine receptor tolerance property" Neuropharmacology, 79:359-367 (2014) (Abstract only)".

Cruz-Trujillo, et al., ""D3 dopamine receptors interact with dopamine D1 but not D4 receptors in the GABAergic terminals of the SNr of the rat" Neuropharmacology, 67:370-378 (2013) (Abstract only)".

Darmopil, et al., ""Genetic inactivation of dopamine D1 but not D2 receptors inhibits L-DOPA-induced dyskinesia and histone activation" Biological Psychiatry, 66(6):603-613 (2009) (Abstract only)".

Dauvilliers, et al., ""Restless legs syndrome: update on pathogenesis" Current Opinion in Pulmonary Medicine, 19(6):594-600 (2013) (Abstract only)".

Deandrade, et al., ""Motor restlessness, sleep disturbances, thermal sensory alterations and elevated serum iron levels in Btbd9 mutant mice" Human Molecular Genetics 21(18):3984-3992 (2012)".

Dinkins, et al., ""Long-term treatment with dopamine D3 receptor agonists induces a behavioral switch that can be rescued by blocking the dopamine D1", Sleep Medicine 40:47-52 (2017)".

Djouhri, et al., ""Spontaneous pain, both neuropathic and inflammatory, is related to frequency of spontaneous firing in intact C-fiber nociceptors" The Journal of Neuroscience, 26(4):1281-1292 (2006)".

Dougherty, et al., ""Properties of mouse spinal lamina I GABAergic interneurons" Journal of Neurophysiology, 94(5):3221-3227 (2005)".

Drago, et al., ""Altered striatal function in a mutant mouse lacking D1A dopamine receptors" Proc Natl Acad Sci USA, 91(26):12564-12568 (1994)".

Dziewczapolski, et al., ""Opposite roles of D1 and D5 dopamine receptors in locomotion revealed by selective antisense oligonucleotides" Neuroreport, 9(1):1-5 (1998) (Abstract only)".

Earley, et al., ""Altered Brain iron homeostasis and dopaminergic function in Restless Legs Syndrome (Willis-Ekbom Disease)" Sleep Medicine, 15(11):1288-1301 (2014) (Abstract only)".

Earley, et al., ""Increased synaptic dopamine in the putamen in restless legs syndrome" Sleep, 36(1):51-57 (2013)".

England, et al., ""L-Dopa improves Restless Legs Syndrome and periodic limb movements in sleep but not Attention-Deficit-Hyperactivity Disorder in a double-blind trial in children" Sleep Medicine, 12(5):471-477 (2011)".

Fiorentini, et al., ""Reciprocal regulation of dopamine D1 and D3 receptor function and trafficking by heterodimerization" Molecular Pharmacology, 74(1):59-69 (2008)".

Garcia-Borreguero, et al., ""Algorithms for the diagnosis and treatment of restless legs syndrome in primary care" BMC Neurology, 11:28 (2011)".

Garcia-Borreguero, et al., ""Augmentation as a treatment complication of restless legs syndrome: concept and management" Movement Disorders, 22(S18):S476-S484 (2007) (Abstract only)".

Garcia-Borreguero, et al., ""Diagnostic standards for dopaminergic augmentation of restless legs syndrome: report from a World Association of Sleep Medicine-International Restless Legs Syndrome Study Group consensus conference at the Max Planck Institute" Sleep Medicine, 8(5):520-53".

Garcia-Borreguero, et al., ""Dopaminergic augmentation of restless legs syndrome" Sleep Medicine Reviews, 14(5):339-346 (2010) (Abstract only)".

Garcia-Borreguero, et al., ""Epidemiology of restless legs syndrome: the current status" Sleep Medicine Reviews, 10(3):153-167 (2006) (Abstract only)".

Garcia-Borreguero, et al., ""Systematic evaluation of augmentation during treatment with ropinirole in restless legs syndrome (Willis-Ekbom disease): results from a prospective, multicenter study over 66 weeks" Movement Disorders, 27(2):277-283 (2012) (Abstract only)".

Garcia-Borreguero, et al., ""The long-term treatment of restless legs syndrome/Willis-Ekbom disease: evidence-based guidelines and clinical consensus best practice guidance: a report from the International Restless Legs Syndrome Study Group" Sleep Medicine, 14(7):675-684 (2013)".

Garcia-Borreguero, et al., ""Treatment of restless legs syndrome with pregabalin: a double-blind, placebo-controlled study" Neurology, 74(23):1897-1904 (2010)".

Garcia-Borreguero, et al., ""Validation of the Augmentation Severity Rating Scale (ASRS): a multicentric, prospective study with levodopa on restless legs syndrome" Sleep Medicine, 8(5):455-463 (2007) (Abstract only)".

Gilbert, et al., ""A D1 receptor antagonist, ecopipam, for treatment of tics in Tourette syndrome" Clinical Neuropharmacology, 37(1):26-30 (2014) (Abstract only)".

Gil-Mast, et al., ""An amino acid residue in the second extracellular loop determines the agonist-dependent tolerance property of the human D3 dopamine receptor" ACS Chemical Neuroscience, 4(6):940-951 (2013)".

Granado, et al., ""D1 but not D4 dopamine receptors are critical for MDMA-induced neurotoxicity in mice" Neurotoxicity Research, 25(1):100-109 (2014)".

Guitart, et al., ""Functional Selectivity of Allosteric Interactions within G Protein-Coupled Receptor Oligomers: The Dopamine D1-D3 Receptor Heterotetramer" Molecular Pharmacology, 86(4):417-429 (2014)".

Hall, et al., ""Changes in mood, depression and suicidal ideation after commencing pregabalin for neuropathic pain" Australian Family Physician, 43(10):705-708 (2014)".

(56) References Cited

OTHER PUBLICATIONS

Han, et al., "'Dopaminergic modulation of spinal neuronal excitability" The Journal of Neuroscience, 27(48):13192-13204 (2007)".
Han, et al., "'Modulation of AMPA currents by D(1)-like but not D(2)-like receptors in spinal motoneurons" Neuroscience, 158(4):1699-1707 (2009)".
Hogl, et al., "'Progressive development of augmentation during long-term treatment with levodopa in restless legs syndrome: results of a prospective multi-center study" Journal of Neurology, 257(2):230-237 (2010)".
Huang, et al., "'Smad3 medlates cardiac inflammation and fibrosis in angiotensin II-induced hypertensive cardiac remodeling" Hypertension, 55(5):1165-1171 (2010)".
Iuga, et al., "'ROS initiated oxidation of dopamine under oxidative stress conditions in aqueous and lipidic environments" The Journal of Physical Chemistry B, 115(42):12234-12246 (2011)".
Johnson, et al., "'The dopamine D3 receptor knockout mouse mimics aging-related changes in autonomic function and cardiac fibrosis" PLoS One, 8(8):e74116 (2013)".
Keeler, et al., "'Opposing aging-related shift of excitatory dopamine D1 and inhibitory D3 receptor protein expression in striatum and spinal cord" Journal of Neurophysiology, 115:363-369 (2016)".
Keeler, et al., "'Increased excitability of spinal pain reflexes and altered frequency-dependent modulation in the dopamine D3-receptor knockout mouse" Experimental Neurology, 238(2):273-283 (2012) (Abstract only)".
Kustermann, et al., "'Depression and attempted suicide under pregabalin therapy" Annals of General Psychiatry, 13(1):37 (2014)".
Kuzhikandathil, et al., "'Activation of human D3 dopamine receptor inhibits P/Q-type calcium channels and secretory activity in AtT-20 cells" The Journal of Neuroscience, 19(5):1698-1707 (1999)".
Kuzhikandathil, et al., "'Identification and characterization of novel properties of the human D3 dopamine receptor" Molecular and Cellular Neurosciences, 26(1):144-155 (2004) (Abstract only)".
Luo, et al., "'The long-term effects of the dopamine agonist pramipexole in a proposed restless legs syndrome animal model" Sleep Medicine, 12(1):41-46 (2010) (Abstract only)".
Machacek, et al., "'Serotonin 5-HT(2) receptor activation induces a long-lasting amplification of spinal reflex actions in the rat" The Journal of Physiology, 537(Pt 1):201-207 (2001)".
Mackie, et al., "'Long-Term Treatment of Restless Legs Syndrome (RLS): An Approach to Management of Worsening Symptoms, Loss of Efficacy, and Augmentation" CNS Drugs, 29(5):351-357 (2015)".
Maggio, et al., "'Heterodimerization of dopamine receptors: new insights into functional and therapeutic significance" Parkinsonism and Related Disorders, 15(Suppl 4):S2-S7 (2009) (Abstract only)".
Malik, et al., "'The effects of dopamine D3 agonists and antagonists in a nonhuman primate model of tardive dyskinesia" Pharmacology, Biochemistry, and Behavior, 78(4):805-810 (2004) (Abstract only)".
Manconi, et al., "'First night efficacy of pramipexole in restless legs syndrome and periodic leg movements" Sleep Medicine, 8(5):491-497 (2007) (Abstract only)".
Manconi, et al., "'Preferential D2 or preferential D3 dopamine agonists in restless legs syndrome" Neurology, 77(2):110-117 (2011)".
Massad, et al., "'Vitamin B-sensitized photo-oxidation of dopamine" Photochemistry and Photobiology, 84(5):1201-1208 (2008) (Abstract only)".
Meneely, et al., "'Differential Dopamine D1 and D3 Receptor Modulation and Expression in the Spinal Cord of Two Mouse Models of Restless Legs Syndrome", Frontiers in Behavioral Neuroscience vol. 12 (2018) 14 pages".
Missale, et al., "'The neurobiology of dopamine receptors: evolution from the dual concept to heterodimer complexes" Journal of Receptor and Signal Transduction Research, 30(5):347-354 (2010) (Abstract only)".
Montplaisir, et al., "'Restless legs syndrome improved by pramipexole: a double-blind randomized trial" Neurology, 52(5):938-943 (1999) (Abstract only)".
Odin, et al., "'Restless legs syndrome" European Journal of Neurology, 9(S3):59-67 (2002) (Abstract only)".
Oertel, et al., "'Long-term safety and efficacy of rotigotine transdermal patch for moderate-to-severe idiopathic restless legs syndrome: a 5-year open-label extension study" Lancet Neurology, 10(8):710-720 (2011) (Abstract only)".
Oertel, et al., "'Rotigotine transdermal patch in moderate to severe idiopathic restless legs syndrome: a randomized, placebo-controlled polysomnographic study" Sleep Medicine, 11(9):848-856 (2010) (Abstract only)".
Oliveira De Almeida, et al., "'The effects of long-term dopaminergic treatment on locomotor behavior in rats" Sleep Science, 7(4):203-208 (2014)".
Paulus, et al., "'Dopamine and the spinal cord in restless legs syndrome: does spinal cord physiology reveal a basis for augmentation?" Sleep Medicine Reviews, 10(3):185-196 (2006) (Abstract only)".
Pham, et al., "'Cu(II)-catalyzed oxidation of dopamine in aqueous solutions: mechanism and kinetics" Journal of Inorganic Biochemistry, 137:74-84 (2014) (Abstract only)".
Phillips, et al., "'Prevalence and correlates of restless legs syndrome: results from the 2005 National Sleep Foundation Poll" Chest, 129(1):76-80 (2006) (Abstract only)".
Picchietti, et al., "'Restless legs syndrome: prevalence and impact in children and adolescents—the Peds REST study" Pediatrics, 120(2):253-266 (2007) (Abstract only)".
Salas, et al., "'All the wrong moves: a clinical review of restless legs syndrome, periodic limb movements of sleep and wake, and periodic limb movement disorder" Clinics in Chest Medicine, 31(2):383-395 (2010) (Abstract only)".
Samir, et al., "'Morphine responsiveness to thermal pain stimuli is aging-associated and mediated by Dopamine D1 and D3 receptor interactions" Neuroscience, 349:87-97 (2017)".
Scholz, et al., "'Dopamine agonists for restless legs syndrome" The Cochrane Database of Systematic Reviews, (3):CD006009 (2011) (Abstract only)".
Scholz, et al., "'Levodopa for restless legs syndrome" The Cochrane Database of Systematic Reviews, (2):CD005504 (2011) (Abstract only)".
Schormair, et al., "'MEIS1 and BTBD9: genetic association with restless leg syndrome in end stage renal disease" Journal of Medical Genetics, 48(7):462-466 (2011)".
Schormair, et al., "'PTPRD (protein tyrosine phosphatase receptor type delta) is associated with restless legs syndrome" Nature Genetics, 40(8):946-948 (2008)".
Shreckengost, et al., "'Bicuculline-sensitive primary afferent depolarization remains after greatly restricting synaptic transmission in the mammalian spinal cord" The Journal of Neuroscience, 30(15):5283-5288 (2010)".
Silver, et al., "'A 10-year, longitudinal assessment of dopamine agonists and methadone in the treatment of restless legs syndrome" Sleep Medicine, 12(5):440-444 (2011) (Abstract only)".
Spieler, et al., "'Restless legs syndrome-associated intronic common variant in Meis1 alters enhancer function in the developing telencephalon" Genome Research, 24(4):592-603 (2014)".
Stefansson, et al., "'A genetic risk factor for periodic limb movements in sleep" The New England Journal of Medicine, 357(7):639-647 (2007)".
Stiasny-Kolster, et al., "'Effectiveness and tolerability of rotigotine transdermal patch for the treatment of restless legs syndrome in a routine clinical practice setting in Germany" Sleep Medicine, 14(6):475-481 (2013) (Abstract only)".
Stiasny-Kolster, et al., "'Low-dose pramipexole in the management of restless legs syndrome. An open label trial." Neuropsychobiology, 50(1):65-70 (2004) (Abstract only)".
Surmeier, et al., "'Coordinated expression of dopamine receptors in neostriatal medium spiny neurons" The Journal of Neuroscience, 16(20):6579-6591 (1996)".
Thorpe, et al., "'Possible sites of therapeutic action in Restless Legs Syndrome: Focus on dopamine and [alpha]2 [delta] ligands" European Neurology, 66(1):18-29 (2011)".
Trenkwalder, et al., "'Restless legs syndrome: pathophysiology, clinical presentation and management" Nature Reviews Neurology, 6(6):337-346 (2010) (Abstract only)".

(56) References Cited

OTHER PUBLICATIONS

Trenkwalder, et al., ""The restless legs syndrome" Lancet Neurology, 4(8):465-475 (2005) (Abstract only)".
Trotti, et al., ""Restless legs syndrome" Handbook of Clinical Neurology, 100:661-673 (2011) (Abstract Only)".
Westrich, et al., ""Development of tolerance in D3 dopamine receptor signaling is accompanied by distinct changes in receptor conformation" Biochemical Pharmacology 79:897-907 (2010)".
Winkelmann, et al., ""Genome-wide association study identifies novel restless legs syndrome susceptibility loci on 2p14 and 16q12.1" PLoS Genetics, 7(7):e1002171 (2011)".
Winkelmann, et al., ""Genome-wide association study of restless legs syndrome identifies common variants in three genomic regions" Nature Genetics, 39(8):1000-1006 (2007) (Abstract only)".
Winkelmann, et al., ""Opioid and dopamine antagonist drug challenges in untreated restless legs syndrome patients" Sleep Medicine, 2(1):57-61 (2001) (Abstract only)".
Winkelmann, et al., ""Sensory symptoms in restless legs syndrome: the enigma of pain" Sleep Medicine, 14(10):934-942 (2013) (Abstract only)".
Xiong, et al., ""Molecular genetic studies of DMT1 on 12q in French-Canadian restless legs syndrome patients and families" American Journal of Medical Genetics Part B: Neuropsychiatric Genetics, 144B(7):911-917 (2007) (Abstract only)".
Xu, et al., ""Dopamine D1 receptor mutant mice are deficient in striatal expression of dynorphin and in dopamine-mediated behavioral responses" Cell, 79(4):729-742 (1994)".
Xu, et al., ""Elimination of cocaine-induced hyperactivity and dopamine-mediated neurophysiological effects in dopamine D1 receptor mutant mice" Cell, 79(6):945-955 (1994) (Abstract only)".
Zeng, et al., ""D3 Dopamine Receptor Directly Interacts With D1 Dopamine Receptor in Immortalized Renal Proximal Tubule Cells" Hypertension 47(part 2):573-579 (2006)".
Zhu, et al., ""Expression and distribution of all dopamine receptor subtypes (D1-D5) in the mouse lumbar spinal cord: A real-time polymerase chain reaction and non-autoradiographic in situ hybridization study" Neuroscience, 149(4):885-897 (2007)".
Zhu, et al., ""Unaltered D1, D2, D4, and D5 dopamine receptor mRNA expression and distribution in the spinal cord of the D3 receptor knockout mouse" Journal of Comparative Physiology A: Neuroethology, Sensory, Neural, and Behavioral Physiology, 194(11):957-962 (2008)".
"Examination Report corresponding to European Application No. 16837850.3 dated Apr. 6, 2021".
"Summons to attend oral proceedings corresponding to European Application No. 16837850.3 dated Sep. 2, 2022".

* cited by examiner

A

B

TREATMENT AND MANAGEMENT OF AUGMENTATION IN RESTLESS LEGS SYNDROME

RELATED APPLICATION DATA

The present application is continuation of and claims priority to U.S. patent application Ser. No. 15/753,149, filed Feb. 15, 2018, which is a 35 U.S.C. § 371 national phase application of International Application Serial No. PCT/US2016/047591, filed Aug. 18, 2016, which claims the benefit, under 35 U.S.C. § 119(e), of U.S. Provisional Application Ser. No. 62/207,225, filed Aug. 19, 2015, the content of each of which is incorporated by reference herein in its entirety.

RESERVATION OF COPYRIGHT

A portion of the disclosure of this patent document contains material, which is subject to copyright protection. The copyright owner, East Carolina University, Greenville, North Carolina, a constituent institution of the University of North Carolina, has no objection to the reproduction by anyone of the patent document or the patent disclosure, as it appears in Patent Office patent files or records, but otherwise reserves all copyright rights whatsoever.

FIELD OF THE INVENTION

The present invention relates to methods of treating Restless Legs Syndrome. Such treatments have the potential to reduce or revert augmentation.

BACKGROUND OF THE INVENTION

Restless Legs Syndrome (RLS) is a sensorimotor disorder that strongly affects, primarily, disrupts sleep [1, 2]. Symptoms include throbbing, pulling, creeping, or other unpleasant sensations in the legs and an uncontrollable urge to move them. These symptoms occur in a circadian fashion and primarily at night, and the sensations range in severity from uncomfortable to irritating to painful [3, 4]. Epidemiologic surveys report a prevalence of RLS between 2.5-10% of the overall population [5-8], making it, with more than 3 million cases in the US alone, the most common movement disorder, and one of the most common sleep disorders.

Several genome-wide association studies have identified genetic markers that are highly expressed in RLS patients [5, 9-13], however, the function of these genes in the nervous system and their contribution to RLS remains unclear. The current primary treatment paradigm for RLS generally focuses on levodopa and dopamine (DA) receptor agonists that target the Gi-coupled inhibitory DA receptors (in particular the subtypes D3R and D2R) [3, 14-18].

Many RLS patients respond robustly to the DA receptor agonists, and D3R agonists can act as early as on the first day of treatment [19]. However, long-term therapy often leads to augmentation and a switch of the initially beneficial actions into adverse effects [20-24]. First described in the therapy of RLS in 1996 [25], augmentation is characterized by an earlier onset of symptoms in the afternoon, a shorter latency to onset of symptoms when at rest, an expansion of symptoms to the upper limbs and the trunk, an overall increase in the intensity of symptoms, including paresthesia [26], and a shorter-lasting therapeutical effect of the medication [27]. Thus DA agonists appear to have a limited period of clinical utility for many patients, and severe augmentation, while not common in the first year of treatment, can develop even after years on the medication [28, 29].

Alternative therapy options, such as alpha-2-delta ligands (gabapentin, pregabalin) have shown promising results in treating RLS symptoms [29-31] and are recommended once DA receptor agonist treatment fails [3, 29], but the side effects of the alpha-2-delta ligands often include dizziness, drowsiness, and difficulty concentrating, and there have been case reports of drug-induced depression [32, 33]. While opioids can also be effective in treating RLS, their usage remains problematic due to the inherent possibility of opioid drug abuse and tolerance [34].

Further, duration and intensity of RLS symptoms are similar to those observed in patients with chronic (neuropathic) pain, and the effectiveness of analgesics in treating RLS supports the concept of an overlap between sensory disturbances in RLS and pain modulatory pathways in chronic pain [35, 36]. Similarly to RLS, chronic pain does not resolve on its own and generally requires long-lasting or life-long treatment, often relying on morphine or its derivatives.

SUMMARY OF THE INVENTION

The present invention provides avenues for the clinical development of alternate treatment options in Restless Legs Syndrome (RLS) that have the potential to reduce or revert augmentation. Further, such treatment options may avoid the side effects reported from other more conventional therapeutic approaches.

Embodiments of the present invention provide a method of treating RLS including administering to a subject an effective amount of a dopamine $D_1$ receptor antagonist.

Embodiments of the present invention also provide a method of treating non-opioid dependent chronic pain including administering to a subject an effective amount of a dopamine $D_1$ receptor antagonist.

Further, embodiments of the present invention provide a method of treating RLS including administering to a subject an effective amount of a dopamine $D_1$ receptor antagonist in combination with a $D_3$ receptor agonist.

Embodiments of the present invention also provide a method of treating non-opioid dependent chronic pain including administering to a subject an effective amount of a dopamine $D_1$ receptor antagonist in combination with a $D_3$ receptor agonist.

Embodiments of the present invention provide a method of preventing nervous system over-excitability including administering to a subject an effective amount of a dopamine $D_1$ receptor antagonist in combination with a $D_3$ receptor agonist, wherein the over-excitability is caused by prolonged exposure to a $D_3$ receptor agonist.

Embodiments of the present invention also provide a method of restoring responsiveness or decreasing tolerance to a $D_3$ receptor agonist, the method including activating a $D_3$ receptor pathway and inhibiting $D_1$ receptor activity after $D_3$ receptor-mediated augmentation.

Embodiments of the present invention provide methods of restoring responsiveness or decreasing tolerance to an opioid agonist, the method including activating a $D_3$ receptor pathway and inhibiting $D_1$ receptor.

Embodiments of the present invention provide a composition including (a) at least one $D_1$ receptor antagonist; (b) at least one $D_3$ receptor agonist; (c) optionally an opioid agonist; and (d) a pharmaceutically acceptable carrier, excipient or diluent.

Embodiments of the present invention provide transdermal delivery systems known in the art, such as patches, bandages, dressing, gauze and the like including a composition including (a) at least one $D_1$ receptor antagonist; (b) at least one $D_3$ receptor agonist; and (c) optionally an opioid agonist.

Embodiments of the present invention provide articles of manufacture such as socks or hosiery including a composition including (a) at least one $D_1$ receptor antagonist; (b) at least one $D_3$ receptor agonist; and (c) optionally an opioid agonist.

Embodiments of the present invention provide a kit including one or more containers having pharmaceutical dosage units including an effective amount of at least one $D_1$ receptor antagonist, at least one $D_3$ receptor agonist and optionally an opioid agonist, wherein the container is packaged with optional instructions for the treatment of restless leg syndrome or non-opioid dependent chronic pain.

The foregoing and other objects and aspects of the present invention are explained in greater detail in reference to the drawings and description set forth herein.

DETAILED DESCRIPTION

Figure 1:
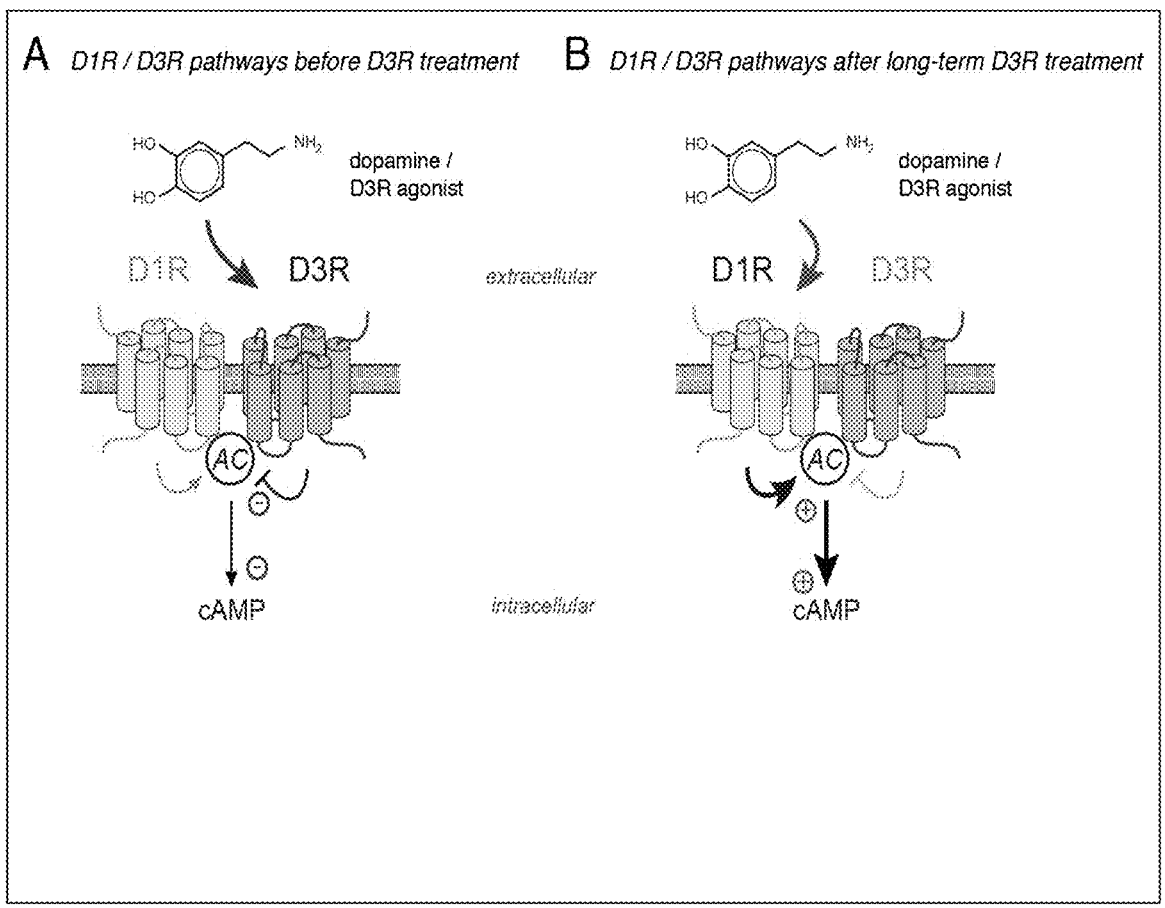
FIG. 1. Proposed model of D1/D3 receptor interactions before and after long-term therapy with D3 receptor agonists in RLS. A: At treatment onset, DA and external D3R agonists (e.g. pramipexole, rotigotine) preferentially target the high-affinity D3 receptor pathway within the D1R/D3R hetero-dimer, and the overall outcome is symptomatic relief. B: With long-term treatment, the D3 receptor becomes sensitized and D1 receptor expression increases, which in turn will increase cAMP levels, PKA activity and overall excitability. We propose that this D3R-dependent but D1R-mediated increase in excitability may underlie augmentation. AC: adenylate cyclase; cAMP: cyclic AMP; (−): inhibitory, (+) excitatory. Adapted from Brewer et al., *Frontiers in Neural Circuits*, 2014 [81].

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

1. Definitions

As used herein, "a" or "an" or "the" can mean one or more than one. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The term "modulate," "modulates" or "modulation" refers to enhancement (e.g., an increase) or inhibition (e.g., a reduction) in the specified activity.

The term "management" as used herein refers to the ability to affect a method, process, state of being, disorder or the like. The effect may be that of prevention, treatment or modulation.

By the terms "treat," "treating" or "treatment of," it is intended that the severity of the disorder or the symptoms of the disorder are reduced, or the disorder is partially or entirely eliminated, as compared to that which would occur in the absence of treatment. Treatment does not require the achievement of a complete cure of the disorder.

By the terms "preventing" or "prevention", it is intended that the inventive methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound being administered.

"Augmentation" refers to a worsening of RLS symptoms that occurs after starting therapy to treat RLS. Signs of augmentation include, but are not limited to, an earlier onset of symptoms (for example, throbbing, pulling, creeping, or other unpleasant sensations in the legs and an uncontrollable urge to move them) which may occur in the afternoon or evening, a shorter latency to onset of symptoms when at rest, an expansion of symptoms to the upper limbs and the trunk, an overall increase in the intensity of symptoms, including paresthesia, and/or a shorter-lasting therapeutical effect of the medication such as tolerance. Augmentation can be mild, moderate or severe.

"Tolerance" refers to a declining response to treatment over time.

"In combination with" means sufficiently close in time to produce a combined effect (that is, in combination with can be simultaneously, or it can be two or more events occurring within a short time period before or after each other). In some embodiments, the administration of two or more compounds in combination with means that the two compounds are administered closely enough in time that the presence of one alters the biological effects of the other. The two compounds can be administered in the same or different formulations or sequentially. Such concurrent administration can be carried out by mixing the compounds prior to administration, or by administering the compounds in two different formulations, for example, at the same point in time but at different anatomic sites or using different routes of administration.

2. Active Agents

Embodiments of the present invention include the use of $D_1$ receptor antagonists. $D_1$ receptor antagonists include, but are not limited to, ecopipam (SCH 39166), SCH 23390, SKF 83566, or mixtures thereof.

Embodiments of the present invention include the use of $D_3$ receptor agonists. $D_3$ receptor agonists include, but are not limited to, nafadotride, PD 128907, pramipexole, pergolide, rotigotine, or mixtures thereof.

Embodiments of the present invention include the use of opioid receptor agonists. Opioid agonists include, but are not limited to, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, or mixtures thereof.

3. Formulations and Administration

In terms of administration, the most suitable route in any given case will depend on the nature and severity of the condition or pharmaceutical formulation being administered. The active agents described herein can be formulated for administration in a pharmaceutical carrier in accordance with known techniques. See, e.g., Remington, *The Science And Practice of Pharmacy* (latest edition).

The compositions of the present invention may be suitable for and formulated for parenteral, oral, inhalation spray, topical (i.e., both skin and mucosal surfaces, including airway surfaces), rectal, nasal, buccal (e.g., sub-lingual), vaginal or implanted reservoir administration, etc. where the most suitable route in any given case will depend on the nature and severity of the condition being treated in combination with the drug profile of the compound described herein as would be understood by one of ordinary skill in the art.

For topical administration, suitable forms include, but are not limited to an ointment, cream, emulsion, microemulsion, a gel, a dispersion, a suspension, a foam, an aerosol, a liquid, a droplet, and suitable transdermal delivery systems known in the art, such as patches and bandages, dressing, gauze and the like including the medicament described herein. Topical administration may further include articles of clothing such as socks or hosiery including the medicament described herein.

The term "parenteral" as used herein includes subcutaneous, intradermal, intravenous, intramuscular, intraperitoneal, intra-articular, intra-synovial, intrasternal, intrathecal, intrahepatic, intralesional and intracranial injection or infusion techniques.

Compositions for injection will include the active ingredient together with suitable carriers including propylene glycol-alcohol-water, isotonic water, sterile water for injection (USP), emulPhor™-alcohol-water, cremophor-EL™, polyvinyl pyrrolidone, lecithin, arachis oil or sesame oil, with other additives for aiding solubility or preservation may also be included, or other suitable carriers known to those skilled in the art. Accordingly, these carriers may be used alone or in combination with other conventional solubilizing agents such as ethanol, propylene glycol, or other agents known to those skilled in the art.

Compositions for oral administration may be, for example, solid preparations such as tablets, sugar-coated tablets, hard capsules, soft capsules, granules, powders, gelatins, and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like.

Where the compounds described herein are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Compositions for nasal administration may be formulated as aerosols, drops, powders and gels. Aerosol formulations typically comprise a solution or fine suspension of the active ingredient in a physiologically acceptable aqueous or non-aqueous solvent. Such formulations are typically presented in single or multidose quantities in a sterile form in a sealed container. The sealed container can be a cartridge or refill for use with an atomizing device. Alternatively, the sealed container may be a unitary dispensing device such as a single use nasal inhaler, pump atomizer or an aerosol dispenser fitted with a metering valve set to deliver a therapeutically effective amount, which is intended for disposal once the contents have been completely used. When the dosage form comprises an aerosol dispenser, it will contain a propellant such as a compressed gas, air as an example, or an organic propellant including a fluorochlorohydrocarbon or fluorohydrocarbon. Compositions suitable for buccal or sublingual administration include tablets, lozenges, gelatins, and pastilles, wherein the active ingredient is formulated with a carrier such as sugar and acacia, tragacanth or gelatin and glycerin.

In particular embodiments, the present invention provides a pharmaceutical formulation including the compound described herein wherein the pharmaceutical formulation is a parenteral formulation. In some embodiments, the parenteral formulation is an intravenous formulation. In some embodiments the parenteral formulation is an intraperitoneal formulation. In other embodiments, the present invention provides a pharmaceutical formulation including the compound described herein wherein the pharmaceutical formulation is an oral formulation.

According to the present invention, methods of this invention include administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the active agents of the present invention can be administered to the subject in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the composition. In some embodiments, the active agents include from about 0.05 to about 95% by weight of the composition. In other embodiments, the active agents include from about 0.05 to about 60% by weight of the composition. In still other embodiments, the active agents include from about 0.05 to about 10% by weight of the composition.

Embodiments of the present invention further provide kits comprising, consisting essentially of or consisting of one or more containers having pharmaceutical dosage units comprising an effective amount of at least one $D_1$ receptor antagonist, at least one $D_3$ receptor agonist and optionally an opioid agonist, wherein the container is packaged with optional instructions for the treatment of Restless Legs Syndrome or non-opioid dependent chronic pain.

"Subjects" as used herein are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, juvenile, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., for prevention and treatment purposes as well as veterinary medicine and/or pharmaceutical drug development purposes. Subjects may include those who are experiencing RLS or are at risk of experiencing RLS. Subjects may also include those who have experienced augmentation previously (with one, two, three, four or more therapies) or those who have not experienced augmentation.

4. Methods of Use

Embodiments of the present invention provide methods of treating or preventing RLS comprising, consisting essentially of, or consisting of administering to a subject an effective amount of a dopamine $D_1$ receptor antagonist. $D_1$ receptor antagonists include, but are not limited to, ecopipam (SCH 39166), SCH 23390, SKF 83566, or mixtures thereof.

Embodiments of the present invention provide methods of treating or preventing non-opioid dependent chronic pain comprising, consisting essentially of, or consisting of administering to a subject an effective amount of a dopamine $D_1$ receptor antagonist. Chronic pain includes, but is not limited to, chronic inflammatory pain, chronic neuropathic pain or a combination thereof.

Embodiments of the present invention provide methods of treating or preventing RLS comprising, consisting essentially of, or consisting of administering to a subject an effective amount of a dopamine $D_1$ receptor antagonist in combination with a $D_3$ receptor agonist. $D_3$ receptor agonists include, but are not limited to, nafadotride, PD 128907, pramipexole, pergolide, rotigotine, or mixtures thereof.

Embodiments of the present invention provide methods of treating or preventing non-opioid dependent chronic pain comprising, consisting essentially of, or consisting of administering to a subject an effective amount of a dopamine $D_1$ receptor antagonist in combination with a $D_3$ receptor agonist.

Embodiments of the present invention provide methods of treating or preventing nervous system over-excitability comprising, consisting essentially of, or consisting of administering to a subject an effective amount of a dopamine $D_1$ receptor antagonist in combination with a $D_3$ receptor agonist, wherein the over-excitability is caused by prolonged exposure to a $D_3$ receptor agonist.

Embodiments of the present invention provide methods of restoring responsiveness or decreasing tolerance to a $D_3$ receptor agonist, the method comprising, consisting essentially of, or consisting of activating a $D_3$ receptor pathway and inhibiting $D_1$ receptor activity after $D_3$ receptor-mediated augmentation.

Embodiments of the present invention provide methods of restoring responsiveness or decreasing tolerance to an opioid agonist, the method comprising, consisting essentially of, or consisting of activating a $D_3$ receptor pathway and inhibiting $D_1$ receptor.

In particular embodiments, the subject is at risk for or suffers from augmentation.

Embodiments of the present invention provide methods of preventing augmentation, in particular, associated with levodopa therapy or dopamine agonist therapy, comprising, consisting essentially of, or consisting of administering to a subject an effective amount of a dopamine $D_1$ receptor antagonist. In some embodiments, the methods of preventing augmentation associated with levodopa therapy or dopamine agonist therapy comprise, consist essentially of, or consist of administering to a subject an effective amount of a dopamine $D_1$ receptor antagonist in combination with a $D_3$ receptor agonist.

In some embodiments of the methods of the present invention, the method further includes administering an opioid receptor agonist. In particular embodiments, the opioid agonist includes, but is not limited to, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, or mixtures thereof.

The effective dosage of any specific active agent will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, administration to a subject such as a human, a dosage of from about 0.01, 0.1, or 1 mg/kg up to 50, 100, or 150 mg/kg or more for each active agent can be employed. Depending on the solubility of the particular formulation of active agents administered, the daily dose can be divided among one or several unit dose administrations.

Having now described the invention, the same will be illustrated with reference to certain examples, which are included herein for illustration purposes only, and which are not intended to be limiting of the invention.

EXAMPLES

Restless Legs Syndrome (RLS): RLS is a common sensorimotor ailment that is not fully understood and, while substantial progress has been made in identifying genetic markers associated with RLS [5, 37-42], its pathophysiological origins remain unclear; this makes it difficult to develop pharmacological treatments that not only cover the symptoms but that might actually 'cure' this disorder. In terms of the underlying neural circuits that play a role in RLS, the most popular theories focus on a dysfunction of the iron system in the basal ganglia, which in turn modifies the dopamine (DA) system [43-46]. However, the basal ganglia play only a minor, if any, role in nociception and pain-signaling pathways, yet the primary symptoms described by RLS patients all focus on altered sensory symptoms that range from discomfort to pain in the affected limbs. The following sensory symptoms must be all present to classify a patient for RLS: 1) an urge to move the legs, accompanied by uncomfortable or unpleasant sensations in the legs; 2) this urge to move begins or worsens during periods of rest or inactivity; 3) this urge to move is partially or totally relieved by movement, at least for the duration of the activity; 4) the urge to move only occurs or is worse in the evening or at night. Finally, 5) none of these criteria may be primary to any other medical condition, such as venous stasis, leg edema, cramps, or similar [47]. The focus on the sensory aspects in RLS points to a role of the spinal cord, as it is the primary linchpin in the nociception and pain-processing pathway [48, 49].

The D3 receptor system: RLS is a chronic disease and is managed with symptomatic medications that are likely to be required for a patient's lifetime [28]. Primary treatment is directed at CNS dopaminergic systems and targets the activation of D2-like receptors (in particular the D3 receptor subtype, D3R). This therapy is usually highly effective and can act as quickly as from the first night of treatment [19]. However, multiple lines of evidence have demonstrated that DA receptor agonists will over time not only lose their efficacy, but also in fact worsen the existing symptoms of RLS, thereby causing augmentation [22, 25, 26, 50]. The D3R is currently the prime target in the treatment of RLS and the D3R preferring-agonists pramipexole and rotigotine have an outstanding efficacy in the initial therapy [14, 19, 51-56]. However, over time these therapies often decrease in their efficacy and lead to adverse effects and augmentation [21, 22, 25, 26, 50].

Diversity of DA receptor actions: DA actions are mediated via both D1-like (D1R, and D5R) and D2-like (D2R, D3R, and D4R) receptors. D1-like receptors are coupled to excitatory GPCR pathways, while D2-like receptors bind to inhibitory GPCRs. Importantly, the D3R can develop an agonist-dependent tolerance phenotype that is accompanied by conformation changes of the receptor [57-60]. It is tempting to speculate that the development of the augmentation observed in RLS patients may be a result of D3R tolerance and its accompanying changes to the second messenger pathway system.

D3R and D1R can display functional interactions that are based on hetero-dimer [61-65] or hetero-tetramer configurations [66]. In the murine spinal cord, D1Rs are prominently expressed in the ventral horn [67, 68], and they are well studied in the context of motor systems. For example, activation of D1Rs tends to increase the excitability or the performance of neural networks that underlie or control fictive locomotion [69-72]. Conversely, D1R antagonists decrease hyper-locomotion in schizophrenia [73], and they are currently being tested in a clinical trial, for treatment of tics in Tourette's syndrome [74, 75]. These latter studies underline the potential role of the D1R antagonists in reducing overall excitability of motor systems, but their possible role in mediating sensory function remains largely unexplored.

The D1 receptor knockout mouse (D1KO): We will use a commercially available transgenic mouse model to test and verify our hypotheses. Originally developed to study the role of the D1R in the striatum [76], the animals are healthy and have no gross abnormalities [77]. Intriguingly, reports indicate the D1KOs show reduced overall motor activities [78, 79].

We previously reported that a dysfunction of the D3R system is associated with a significant decrease in thermal pain withdrawal latencies in the intact animal, which was in the isolated spinal cord accompanied by a decrease in C-fiber mediated frequency-adaptation [80]. These data suggested that the D3R has an important role in the control of pain modulation, and we proposed the D3R knockout mouse (D3KO) as a possible model for increased nociceptive sensitivity. In a subsequent study we presented evidence that D3KOs have increased D1R protein expression levels in the spinal cord, the primary processing and integration site of the nociceptive pathway, and we proposed a model in which the dysfunction of the D3R system leads to an upregulation of the D1R pathway [81], a modification of which laid the groundwork for the present study (FIG. 1).

Figure 2:
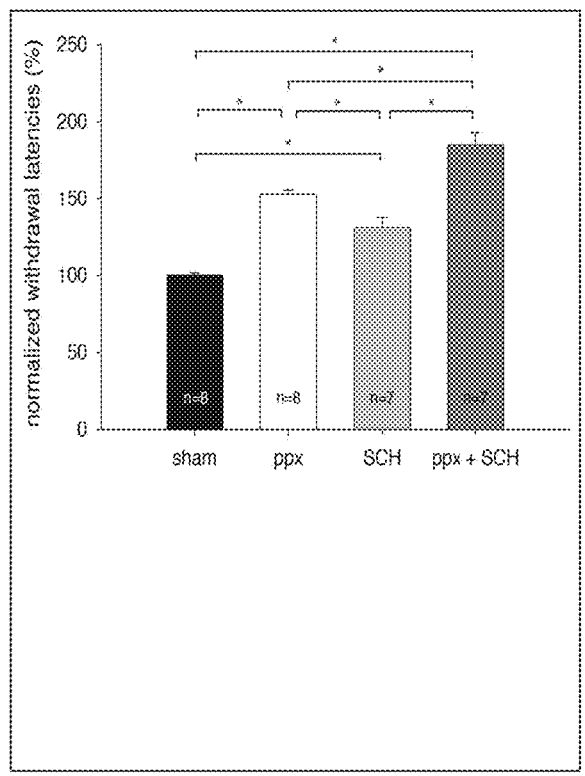
FIG. 2. Acute modulation of thermal withdrawal responses by D3R agonist (pramipexole, ppx) and D1R antagonist (SCH 39166). Both drugs have a similar effect on behavioral outcome and increase withdrawal latencies, suggesting an analgesic effect (white and light gray bar). A combination treatment with both drugs significantly increases withdrawal latencies over those of each drug alone, suggesting a synergistic effect.

RLS is symptomatically treated with D3R agonists that lose their efficacy over time, leading to augmentation. We therefore first tested the effects of D3R agonists used in the clinic on pain withdrawal reflexes in an acute setting, in wild type (WT) animals and then assessed the effects of an acute block of D1R function in the same animals (FIG. 2).

Example 1

Test the Hypothesis that Long-Term Treatment with D3R Agonists in the Intact Animal Leads to Augmentation that can be Restored by Block of D1R Function The objective of these studies is to establish the role of the dopamine D1 receptor system in the emergence of D3 receptor-agonist induced augmentation. The working hypothesis is that continuous long-term application of a D3 receptor agonist will invoke a switch from inhibition to excitation. Specifically, we will treat animals with D3 receptor agonists currently used to treat RLS (e.g., pramipexole and rotigotine) and assess the effects of these compounds on leg withdrawal latencies when the animals are subject to a painful thermal stimulus. We predict that the initially analgesic effect (extending withdrawal latencies) of the D3Rs will be replaced over time by a hyperalgesic effect (decrease in withdrawal latencies).

Figure 3:
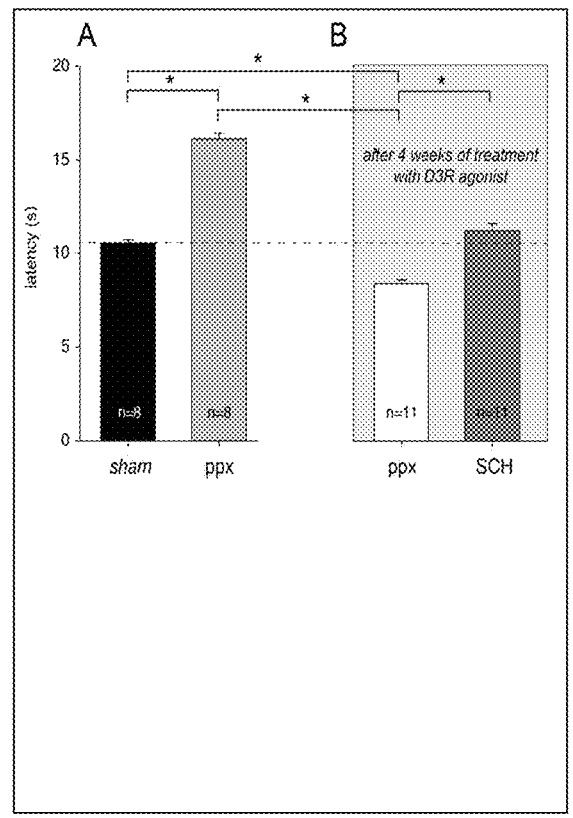
FIG. 3. Opposite modulatory effects of acute vs. long-term D3R activation. Following the acute effect (A), long-term treatment with a D3R agonist (>4 weeks, B), led to a decrease in thermal withdrawal latencies, suggesting an increase in sensitivity. This hyperalgesic effect mimics the augmentation phenotype in RLS FIG. 4. D1R protein expression in the spinal cord is increased after prolonged in vivo treatment with a D3R agonist.

We found that both D3R agonist and D1R antagonist increased thermal withdrawal latencies (pramipexole [ppx]; 0.5 mg/kg: to 152.9+/−2.8% of control; SCH 39166; 0.1 mg/kg: to 131+/−6.5% of control). The combination treatment of ppx and SCH 39166 further increased the latencies to 185+/−7.9% of control (p=0.001, RM ANOVA). These data support the hypothesis that nociception is mediated by means of both D3R and D1R pathways. Next we tested the effects of extended exposure to a D3R agonist in WT, and the consequence of a block of D1R function after this long-term exposure (FIG. 3). Withdrawal latencies were tested on day 1 (light gray bar in FIG. 3, panel A) and at the end of a 4-week long experiment, in which animals were subject to daily i.p. injections (7 days/week, white bar in FIG. 3, panel B). We found that this continuous exposure to the D3R agonist not only reduced withdrawal latencies significantly in comparison to the single D3R agonist exposure on day 1, but that it was sufficient to induce a switch from the acute analgesic effect to a hyperalgesic response when compared to sham (black bar in FIG. 3, panel A), suggesting an increase in C-fiber mediated thermal sensitivity.

Figure 4:
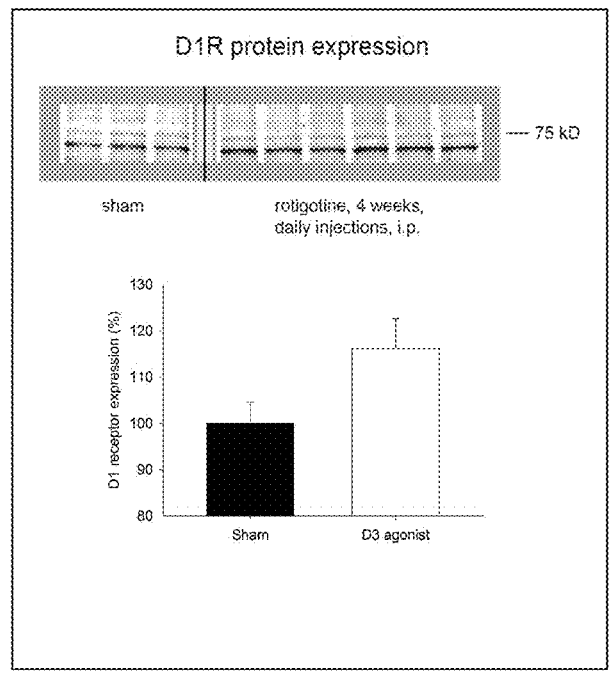

Moreover, subsequent block of D1R function significantly increased withdrawal latencies and brought them back to control values obtained prior to the onset of the experiment (FIG. 3, panel B). This rescue from the 'hyperalgesic' state suggests that D1R function or levels may be upregulated in the D3R-treated animals. To test this hypothesis, we measured D1R protein expression levels in the lumbar spinal cord. We found that the repeated i.p. injections of the D3R agonist led in the treated animals to an increase in D1R protein expression (FIG. 4).

Together, these data suggest that the systemic application of the D3R agonist can lead to two different outcomes, depending on the time frame of the treatment: Acute application can have fast acting analgesic effects, as it significantly increases thermal withdrawal reflex latencies and thus decreases thermal pain sensitivity. In contrast, longer-lasting treatments with the D3R agonist can lead to the opposite effect, i.e., a decrease of withdrawal latencies and thus an increase in thermal pain sensitivity. These data suggest that our mouse model with the extended D3R agonist exposure might be an appropriate representation of the augmented phenotype in RLS.

The role of short- and long-term exposure to D3R agonists and D1R antagonists and their interactions on thermal (pain fiber-associated) reflexes in vivo is to be addressed and evaluation post mortem of the corresponding changes to DA receptor protein expression in the immunohistological profile of the spinal cord in vitro.

Animals: We will use 3-4 months old male C57BL/6 wild type (WT) and D1 receptor knockout mice (D1KO; B6.129S4-Drd1a$^{tm1Jcd}$/J, Jackson Laboratories) for this proof-of-concept study. Based on our past experience and a power analysis, we expect to use for this aim in a best-case scenario 120, and in a worst-case scenario 160 animals of each WT and D1KO strain (240-320 animals total). Within each strain, animals will be serendipitously grouped and evenly distributed into 4 cohorts with 5 subgroups (a-e), and 6-8 animals/subgroup (s. flow chart in FIG. 5).

Assessment of baseline pain withdrawal reflex latencies ("thermal pain"): RLS is first and foremost a sensory disorder that is accompanied by a motor component. The clinical sensations ("urge to move") stem from deep muscle tissues and are considered "painful" by many, if not most patients, unless acted on immediately (moving of the limbs). Pain from deep muscles is carried by both unmyelinated C-fibers (both peptidergic and non-peptidergic) as well as a-∂ fiber. Pain due to thermal stimulus energy is carried specifically by subsets of these nociceptors that express the transient receptor potential-V1 protein (TRPV1). These TRPV1 expressing nociceptors also have extensive cutaneous distribution and are easily activated by a heat source applied to the surface of the skin. Thus the thermal pain stimulus tested in the Hargreaves apparatus (IITC, Inc., Life Science, Model 39D) provides an appropriate surrogate for monitoring changes in deep muscle nociceptor activity that may be present in RLS, and the latencies to withdraw the hindpaw from a noxious thermal stimulus applied to the plantar surface of the hindpaw provide a measure of pain sensitivity. Animals will be removed from their home cages and placed individually in the small Plexiglas containers of the Hargreave's system (4" width×4" length×5" height). The behavior room has optional low light settings to minimize visual perturbations. Each day, animals will be acclimatized on the Hargreaves platform for 1-2 hrs. Subsequently, baseline withdrawal latencies will be determined for each animal, with five independent trials performed per hindpaw per session and a mean latency calculated for each day. The tests will be administered over 4 days.

Figure 5:
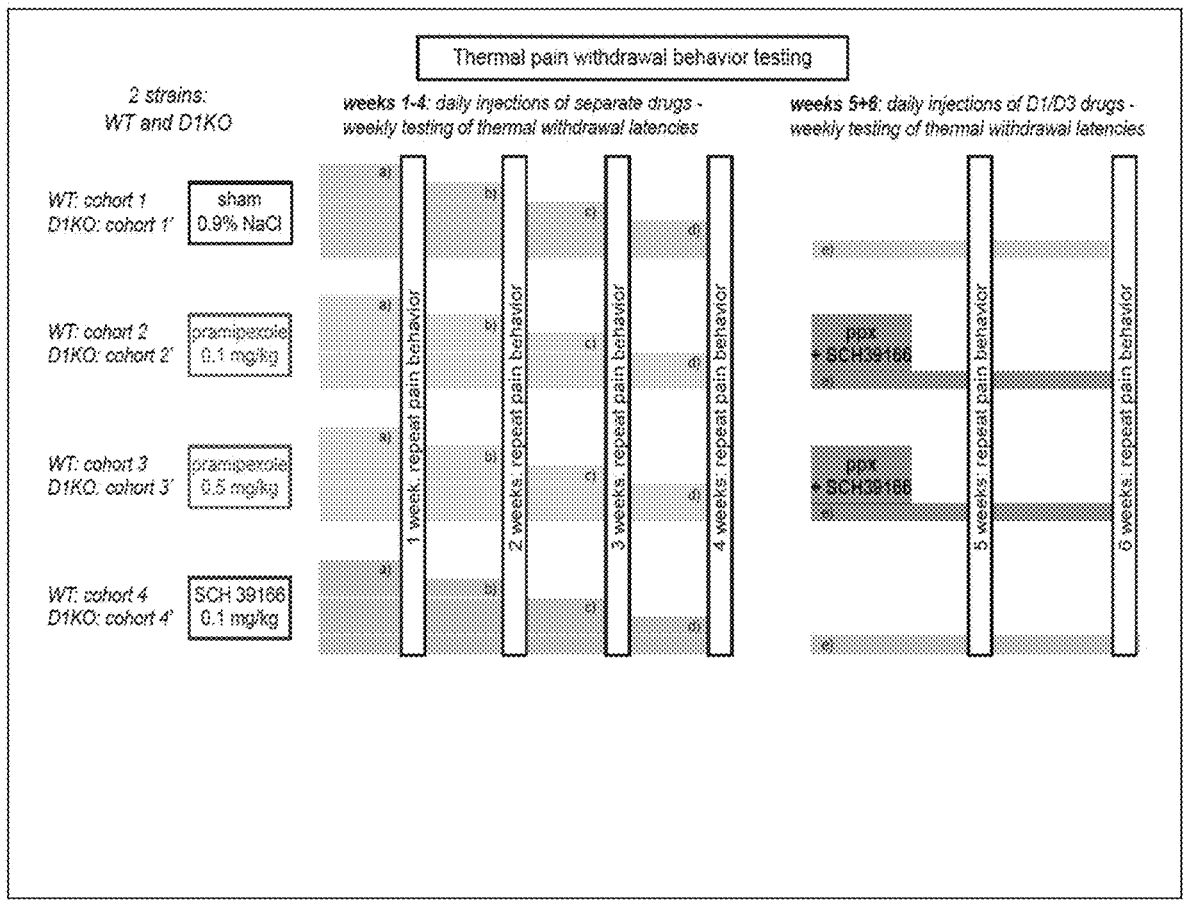
FIG. 5. Flowchart of experimental design. Thermal pain withdrawal reflexes will be tested in wild type (WT) and D1 receptor knockout (D1KO) animals. Each strain will consist of 4 cohorts and 5 subgroups (a-e) that will undergo different drug injection paradigms (sham vs D3R agonist [at 2 doses] vs D1R antagonist). Pain withdrawal reflexes will be tested daily and animals of the subgroups a-d will be sacrificed after behavioral testing and their spinal cords collected. Subsets (e) of each cohort will continue to receive daily injections and thermal pain reflexes will be tested after weeks 5 and 6. Starting in week 5, cohorts 2 and 3 will receive the D3R agonist/D1R antagonist combination treatment and their responses will be compared to the corresponding subgroups of cohorts 1 (sham) and 3 (SCH 39166).

Drug injection protocol: After establishing baseline parameters, each animal will receive in weeks 1-4 once daily a single-drug i.p. injection of the respective compound: 0.9% NaCl (sham), the D3R agonist (pramipexole) at 0.1 or 0.5 mg/kg, or the D1R antagonist ecopipam (SCH 31966) at 0.1 mg/kg, and tested for thermal pain withdrawal tolerance (details in flow chart, FIG. 5). At these concentrations, we observed in our preliminary studies changes in both behavior and receptor protein expression that we will continue to explore in more detail here. Each cohort will be treated independently of each other, but all animals will receive their respective i.p. injections daily (7 days/week) between 9-11 am in the morning, to avoid possible conflicts with the circadian cycle [82]. Thermal pain withdrawal reflexes will be tested as above on 4 subsequent days per week in the afternoon, starting on the second day of the drug injections. Subgroups a) of each cohort will be euthanized after 1 week, with subgroups b)-d) following suite in 1-week intervals (FIG. 5).

After week 4, subsets (e) of cohort 1 and 4 will continue to receive their respective single-drug dose injections (sham vs. SCH 39166) and tested as before in weeks 5 and 6 before being sacrificed after week 6. In contrast, animals in cohorts 2 will receive a two-drug paradigm in a single injection, including pramipexole (0.1 mg/kg)+SCH 39166 (0.1 mg/kg), while animals in cohort 3 will receive pramipexole (0.5 mg/kg)+SCH 39166 (0.1 mg/kg). Behavioral testing will be performed as with animals in cohorts 1 and 4. At the end of the 6 weeks, animals will be deeply anesthetized and euthanized.

Tissue Collection and Analysis: Two hours after the conclusion of the last behavioral test in each week and subgroup, animals will be deeply anesthetized with inhaled isoflurane (4-5%), decapitated, and their spinal cords dissected out, sliced horizontally to separate dorsal and ventral parts, frozen in liquid nitrogen, and stored at −80° C. Proteins will be homogenized in RIPA buffer containing protease and phosphatase inhibitors (Sigma-Aldrich, St. Lois, MO), the lysates centrifuged, and the supernatant collected. Total protein will be quantified using an EZQ Quantitation Kit (R33200; Invitrogen, Grand Island, NY). Equal concentrations of protein will be separated using a SDS-PAGE (Criterion TGX Any kD, Bio-Rad, Canton, MA) and transferred onto a PVDF membrane (Immobolin-P, Millipore, Germany). To verify consistent protein transfer across the lanes, we will measure total protein staining of the membrane with Coomassie Blue in the corresponding lanes.

According to preliminary findings, prolonged D3R agonist treatment alters thermal reflex responses in the hindlimbs, which are mediated in the lumbar spinal cord. Thus we will test D1R and D3R protein expression in this specific part of the CNS. For D1R protein assessments, membranes will be blocked overnight using 5% BSA at 4° C. and probed with primary antibodies for the D1R (ab81296, Abcam, Cambridge, Mass,) at 1:1000 overnight. We have verified this antibody in control experiments with brain tissues from D1R knockout mice (D1KO; donated by Dr. Rosario Moratalla, Cajal Institute, Madrid, Spain [83]). Membranes will be washed 4× at 5 minutes in TBS-T and incubated for 30 minutes at room temperature using 5% BSA in anti-rabbit IR800 (35571, Thermo Scientific, Rockford, IL) and anti-mouse IR680 (926-68070, Li-Cor, Lincoln, NE) secondary antibodies at 1:30000. The membranes will then be washed another 3× for 5 min in TBS-T followed by 2 washes at 5 min in PBS. Target proteins will be visualized using the Li-Cor detection system (Odyssey Clx, Li-Cor Biosciences, Lincoln, NE) and analyzed with the associated software (Image Studio, Li-Cor) or with ImageJ (NIH). D1R protein expression values will then be normalized to total protein expression (Coomassie). For the assessment of D3R protein expression, we will follow the same protocol, but probe with a primary antibody for the D3R instead (ab42114, Abcam).

Anticipated results (in vivo): Our preliminary in vivo data that stem from two time points only (acute treatment and after long-term D3R exposure, FIGS. 2 and 3 indicate not only the feasibility of our approach but also suggest a likely favorable outcome. We expect to:

1) establish in WT mice that continuous treatment with a D3R agonist will lead to two different behavioral outcomes when testing for thermal pain sensitivity: short-term application (less than 1-2 weeks) will result in an increase in withdrawal latencies, indicating a decreased sensitivity and thus an analgesic effect of the drug. In contrast, longer-term application (3-4 weeks) will gradually reverse this effect and lead to a progressive decrease in withdrawal latencies and increased sensitivity, indicating an abnormally heightened sensitivity to the thermal stimulus applied. We expect that this switch in behavioral outcome will mimic the outcomes of augmentation reported in the clinic. We further predict that this switch will be dose-dependent, and that the low dose pramipexole treatment (0.1 mg/kg) applied to cohort 2 will require a longer time to develop the switch, possibly into weeks 3 and 4.

2) establish in WT that adjuvant treatment with the D1R antagonist SCH 39166 (ecopipam) to cohorts 2 and 3 will reverse their 'augmented' state in thermal pain sensitivity and return withdrawal latencies to those observed in controls and/or those observed during the initial treatment with the D3R agonists.

3) establish that D1KO animals will respond to the D3R agonist (cohorts 2' and 3') throughout the 4-week treatment with a persistent increase in pain withdrawal latencies, without a switch to an 'augmented' state and that this effect will be dose-dependent of low or high pramipexole concentrations.

4) establish that the switch to the 'augmented' state is dependent on the D1 receptor, as the D1KO will not change their responses to the D3R agonist over time.

Anticipated results (in vitro): We can readily detect changes in DA receptor expression in the spinal cord [81]. We predict that the behavioral responses observed will be mirrored by changes in D1R and D3R protein expression in the spinal cord. Specifically, we expect that short-term (1-2 weeks) treatment will lead in cohorts 2 and 3 to a dose-dependent increase in D3R expression, and a parallel decrease in D1R protein expression. We anticipate that this shift in protein expression levels will reverse in weeks 3 and 4, with D1R levels increasing and D3R levels decreasing.

Statistical Analysis: For the behavioral experiments, withdrawal latencies under drug conditions will be averaged and normalized to the mean of the pre-drug values, and statistical significance will be determined with RM ANOVA and subsequent post-hoc comparisons, as appropriate, and with a set <0.05 (SigmaPlot, Systat, San Jose, CA). For the data analysis of the Western blots, we will use One-way ANOVA testing to assess significance, and identify group differences with appropriate post-hoc comparisons (e.g. Holm-Sidak).

Example 2

Test the Hypothesis That the Isolated Spinal Cord Contains all the Necessary Building Blocks to Induce, and Recover from, D3R Agonist-Mediated Augmentation The objective of this study is to establish that the isolated spinal cord houses the necessary cellular machinery and neural circuitry to implement the D3R agonist-induced modulatory changes that lead to the behavioral changes observed in vivo. We will test the hypothesis that prolonged bath-application of a D3R agonist will induce a biphasic (from inhibitory to excitatory) modulatory response in the isolated spinal cord. Specifically, we will assess the changes in spinal reflex amplitudes (SRAs), using the monosynaptic stretch reflex in the lumbar spinal cord as a model of neural circuit function. We predict that D3R application will initially reduce SRAs in WT and D1K0 animals alike, and that this modulatory effect will gradually switch over time in WT alone to then increase SRAs. The rationale of this aim is to show that the neural circuitry in CNS and in particular the spinal cord is sufficient to account for the behavioral changes observed in the intact animal.

A prime concern in the therapy with any drug is the development of unwanted or harmful side effects. The system-wide application of any medical compound that is taken up either orally, by injection or through the skin via a slow-release patch can have effects on multiple organ tissues.

RLS is a neurological disorder in which the spinal cord serves as the first integration site of the sensory symptoms and it provides a unique neural circuit, the monosynaptic stretch reflex, that can be isolated, identified, and kept functionally alive in the isolated spinal cord in vitro to test the actions of select neurotransmitters and modulators on this circuitry [92-95]. The experiments will take advantage of this accessibility and functionally and determine the actions and the time course of D3R agonist actions on SRAs with extracellular stimulation and recording techniques. This will establish if the opposite modulatory D3R agonist actions observed in the clinic and in our in vivo approach can arise from within the CNS alone.

Figure 6:
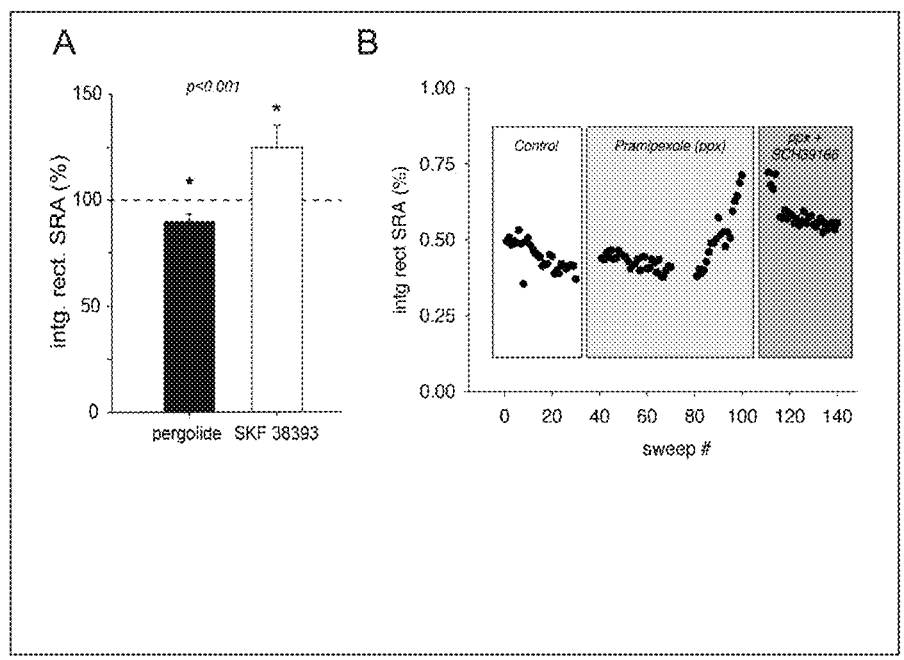
FIG. 6. D3R and D1R agonist modulation of spinal reflex amplitudes (SRAs). A. Short-term bath application (less than 30 min) of the D3R agonist pergolide significantly decreases SRAs over control. In contrast, application of the D1R agonist, SKF 38393, increases SRAs. B. Continuous longer-lasting exposure to the D3R agonist, pramipexole (ppx), invokes, after an initial decrease, a strong increase in SRA amplitude. This increased SRA can then be decreased by additional bath-application of a D1R antagonist (SCH 39166).

We have shown in our published work that DA has a dose-dependent effect on a spinal central pattern generator, with low-dose and inhibitory actions mediated via D2-like receptors (including D3R), while high dose and excitatory actions were mediated via D1Rs [69]. We present here data that support these different modulatory actions, and we can show that activation with the D3R agonist, pergolide, significantly decreased SRAs while D1R activation with SKF 38393 significantly increased them (FIG. 6, panel A). More importantly, we found that prolonged activation of the D3R in the isolated spinal cord (>3 hrs) led to a subsequent increase in SRA, which we could reverse with the addition of a D1R antagonist to the bath (FIG. 6, panel B).

Animals: We will use young, neonatal WT and D1KO pups of either sex, aged 5-14 days.

Experimental Design:

Animals will be anesthetized with ketamine/xylazine and decapitated, and the spinal cord carefully dissected out of the body cavity and placed in a Sylgard-lined (Dow Corning, Midland MI) Petri dish in cooled (<4° C.) artificial cerebrospinal fluid (ACSF) containing (in mM); 125 NaCl, 2.5 KCl, 2 $CaCl_2$, 1 $MgCl_2$, 25 glucose, 1.25 $NaH_2PO_4$, and 26 $NaHCO_3$ at a pH of 7.4, oxygenated with 95% $O_2$-5% $CO_2$. After opening and removing the dura mater, to facilitate the access of ACSF to the cord, dorsal and ventral roots will be identified and pinned out with small insect pins. Preparations will either be left intact (in animals less than 7 days old) or hemisected mid-sagittally (>1 week old animals) [80, 92]. The hemisection in the older animals helps better oxygenate the tissue and extends the life expectancy of the isolated preparation. Under these conditions, we can hold the spinal cord functionally alive for more than 24 hours, and we have been able test SRAs in individual preparations for up to 48 hours. After a 30-60 min recovery at room temperature, glass suction electrodes will be placed on the distal parts of dorsal and ventral roots of lumbar segments L2-L5. After establishing the stability of the electrode connections to the roots, dorsal roots will be stimulated with current pulses of 250-500 µA amplitude and 100-500 µs duration, to activate low-threshold Aβ- and high-threshold and pain-associated Aδ and C-fibers, and we will record the associated reflex responses (monosynaptic stretch reflex, MSR; and longer-latency, LLR) on ventral roots with a Digidata 1440 using pClamp 10 software (Axon Instr., Union City, CA, USA) [13, 80]. SRA recordings will last 30 min per epoch, and epochs will be repeated as needed, to include and compare later modulatory actions with those from earlier ones. For the analyses, reflex responses will be rectified and the calculated integrals of these responses measured and compared between epochs of identical duration before and after drug application. For short-term assessments of drug effects, we will average the last ten consecutive SRAs measured before drug application with the last ten consecutive SRAs after 30 min of application of the drugs per epoch. After establishing baseline recordings, we will bath-apply select D1R and D3R compounds (D1R: SKF 38393 [agonist] and SCH 39166 [antagonist]; D3R: pramipexole, rotigotine [agonists], and SB27701A [antagonist]) at concentrations of 0.1-10 µM. We will first test their individual modulatory actions on SRAs over short (less than 30 min) and longer periods of time (up to 24 hrs). Following the evaluation of the modulatory effects of the individual drugs, we will pair the applications of D1R and D3R agonists/antagonists. We will apply drug-combinations of D3R agonists and D1R antagonist or D3R antagonist and D1R agonist to assess the functional interactions between these two receptors in vitro.

We expect that in the isolated WT spinal cord, short-term application of the D3 agonists will lead to a decrease of SRAs in a dose-dependent manner. We expect that this modulatory effect will be similar in the D1KO spinal cord, suggesting that D3R function remains functional in D1KO. We anticipate that prolonged activation of the D3R will lead in WT to a reversal of the initial response while it will not further change SRAs in D1KO. We further expect that the highly selective D3R antagonist, SB 27701-A [96], will increase SRAs during the initial application window in both WR and D1KO alike and that this modulatory effect will not change over time in WT or D1KO. We forecast that bath-application of the D1R antagonist will decrease SRAs in WT but not D1KOs, and that activation of the D1R in the WT spinal cord will reverse the long-term D3R agonist-induced increase in SRA. Together, these data will show that both D3Rs and D1Rs are necessary to induce the switch to the 'augmented' state, and that the spinal reflex in the spinal cord could be target that, in vivo, might mediate similar actions. Our data will also indicate that block of D1R function at the neural circuit level will be sufficient to reverse the switch from inhibition to excitation during the prolonged exposure of the cord to D3Rs. In conjunction with other studies, these studies will support our hypothesis that D3R agonist-induced augmentation in RLS patients may be rescued by the adjuvant treatment with a D1R antagonist.

Statistical Analysis: For the experiments on the isolated spinal cords, we will measure SRAs under control and drug conditions, and data will be averaged and normalized to the mean of the pre-drug values. Statistical significance will be determined with One-Way ANOVA and subsequent post-hoc comparisons or t-tests, as appropriate, and with a set <0.05 (SigmaPlot, Systat, San Jose, CA).

Example 3

Changes in Thermal Withdrawal Latencies Over Time with Chronic Injections

Figure 7:
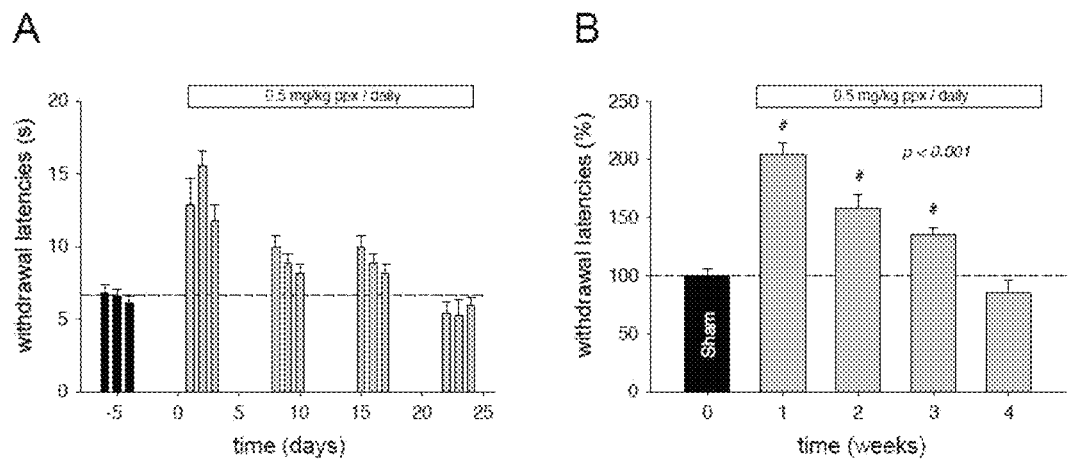
FIG. 7. Changes in thermal withdrawal latencies over time with chronic injections. Testing with the second most-used treatment option for RLS, pramipexole (0.5 mg/kg/day) is shown and an established the time course of the switch from analgesia to hyperalgesia. A depicts the results of the daily measurements, and B shows the weekly averages.

We had previously tested only the effects of the D3R agonist, rotigotine (Neupro). Here we added testing of the second most-used treatment option for RLS, pramipexole (0.5 mg/kg/day), and we also established the time course of the switch from analgesia to hyperalgesia (FIG. 7). FIG. 7, panel A depicts the results of the daily measurements, and FIG. 7, panel B the weekly averages. We found that withdrawal latencies to a thermal stimulus significantly increased in week 1 to 204.81%±6.3% of control (FIG. 7, panel B). This analgesic effect decreased in weeks 2 (158+/−12% of control) and 3 (135+/−6.5% of control) but was completely lost in week 4 (85+/−11% of control).

Example 4

Figure 8:
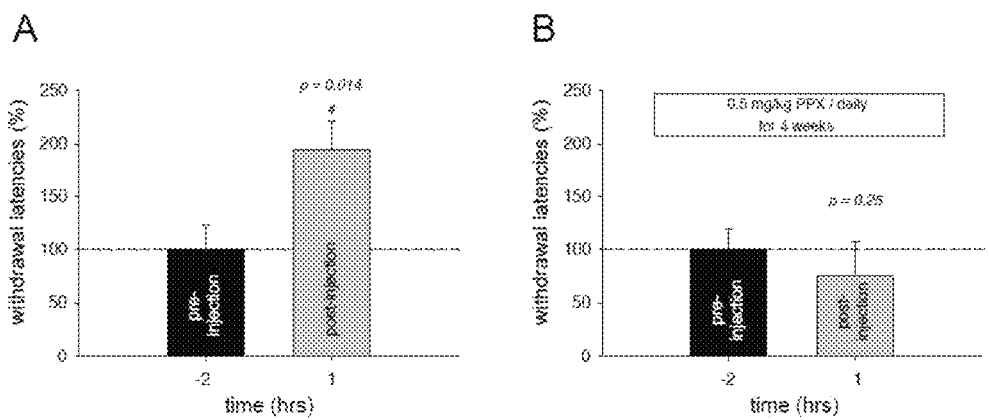
FIG. 8. Changes in thermal withdrawal latencies pre and post injections with pramipexole. Animals were tested before and after a single injection of a D3R Agonist (0.5 mg/kg pramipexole) both before the first injection in week 1 and immediately before the last injection, after 4 weeks to show the short term effects of the drug. A shows the immediate benefits that a single shot of the D3R Agonist had on withdrawal latencies. B shows results after 4 weeks of daily injections with pramipexole.

Changes in Thermal Withdrawal Latencies Pre and Post Injections with Pramipexole Animals were tested before and after a single injection of a D3R Agonist (0.5 mg/kg pramipexole) both before the first injection in week 1 and immediately before the last injection, after 4 weeks. This was done to show the short term effects of the drug. FIG. 8, panel A shows the immediate benefits that a single shot of the D3R Agonist had on withdrawal latencies. Pre-injection withdrawal latencies of week 1 acted as a baseline and was recorded to be 99.97%±22.8%. Post injection withdrawal latencies of week 1 significantly, one hour after the first injection, increased to 194.65%±27% (p=0.014, t-test). In contrast, as shown in FIG. 8, panel B, after 4 weeks of daily injections with pramipexole, the compound has completely lost its initial efficacy, and even shows a trend to a decrease (pre-injection: 99.98+/−19.%; 1 hr post-injection: 75.2+/−32%), which was not significantly different from pre-injection (p=0.25).

Example 5

Changes in Thermal Withdrawal Latencies Pre and Post Injections with D1R Antagonist SCH 39166

Figure 9:
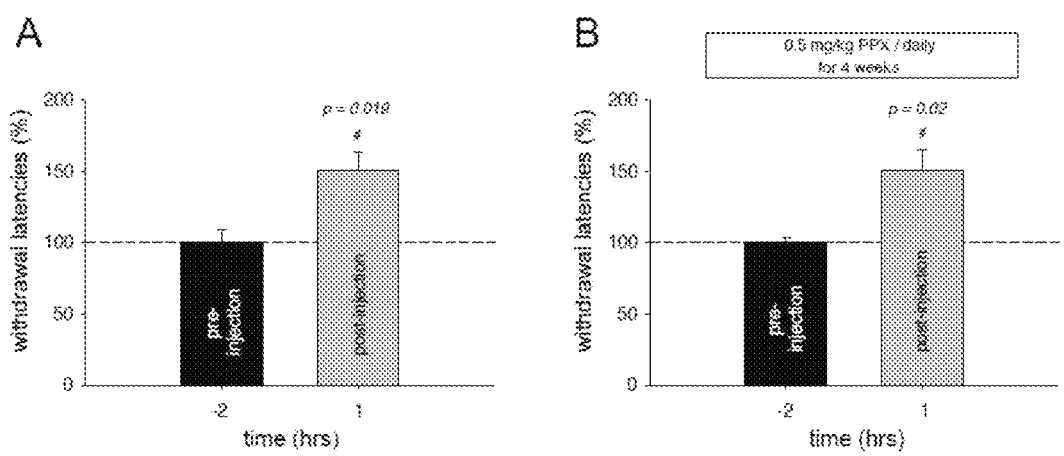
FIG. 9. Changes in thermal withdrawal latencies pre and post injections with D1R Antagonist SCH 39166. Animals were tested before and after a single injection of a D1R Antagonist, at the beginning of the study (in week 1, A), and after the 4-week drug paradigm as shown in B.

Animals were tested before and after a single injection of a D1R Antagonist, at the beginning of the study (in week 1, FIG. 9, panel A), and after the 4-week drug paradigm (FIG. 9, panel B). This was done to show the ability that a D1R antagonist maintains its capability to achieve a modulatory (analgesic) benefit, even in the absence of a D3 receptor agonist effect. We found that injection withdrawal latencies of the non-treated group (FIG. 9, panel A) increased withdrawal latencies from 100.01% ±8.7% (control) to 151 +/−13% one hour after the injection (p=0.019, t-test). This strong and significant effect was maintained in the animals treated for 4 weeks with the D3 receptor agonist, pramipexole (FIG. 9, panel B, pre-injection: 99.9 +/−3%, 1 hour post-injection: 150.+/−15%, p=0.02.

Example 6

Long Term Testing of Drugs and Drug Combinations on Withdrawal Latencies

Long-term (daily for 4 weeks) testing of the effects of the following drugs and drug combinations on withdrawal latencies: a) rotigotine (D3 receptor agonist), to repeat the time course experiments with another D3 agonist; b) D1 receptor antagonist (SCH 39166), to test if continued block of the D1R has any adverse side effects; and c) a combination treatment of D1R antagonist+D3R agonist, to test if augmentation can be prevented. Our current data sets indicate that the D3R agonist and the (D1/D3) combination treatment have a similar analgesic effect, while the D1 antagonist on its own does not have a significant effect.

Example 7

Time Course Studies

Figure 10:
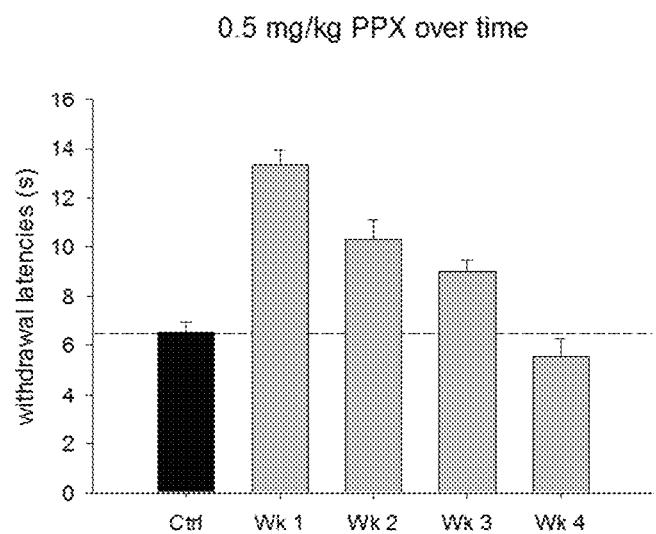
FIG. 10. D3R agonist, pramipexole (PPX) was tested and a gradual time course of the behavioral changes was established as shown in A. B shows that the responsiveness of the animals to a single treatment with the D1R antagonist rescues the original D3-induced inhibition in "augmented" animals.
Figure 10:
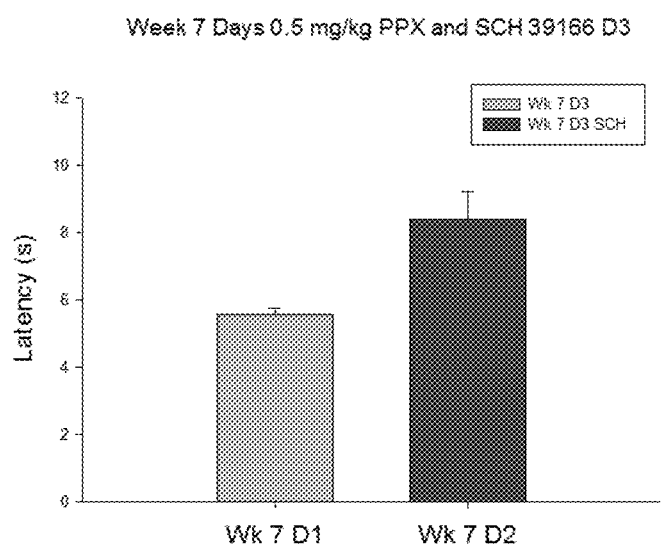

The second most-used D3R agonist, pramipexole (PPX) was tested and a gradual time course of the behavioral changes during this treatment was established (FIG. 10, panel A), and this study shows that the responsiveness of the animals to a single treatment with the D1R antagonist rescues the original D3-induced inhibition in "augmented" animals (FIG. 10, panel B).

The foregoing is illustrative of the present invention, and is not to be construed as limiting thereof. The invention is defined by the following claims, with equivalents of the claims to be included therein.

Bibliography:
1. Erman, M. K., *Selected sleep disorders: restless legs syndrome and periodic limb movement disorder, sleep apnea syndrome, and narcolepsy.* Psychiatr Olin North Am, 2006. 29(4): p. 947-67; abstract viii-ix.
2. Chahine, L. M. and Z. N. Chemali, *Restless legs syndrome: a review.* CNS Spectr, 2006. 11(7): p. 511-20.
3. Earley, C. J., *Latest guidelines and advances for treatment of restless legs syndrome.* J Olin Psychiatry, 2014. 75(4): p. e08.
4. Odin, P., M. Mrowka, and M. Shing, *Restless legs syndrome.* Eur J Neurol, 2002. 9 Suppl 3: p. 59-67.
5. Dauvilliers, Y. and J. Winkelmann, *Restless legs syndrome: update on pathogenesis.* Curr Opin Pulm Med, 2013. 19(6): p. 594-600.
6. Phillips, B., et al., *Prevalence and correlates of restless legs syndrome: results from the 2005 National Sleep Foundation Poll.* Chest, 2006. 129(1): p. 76-80.
Garcia-Borreguero, D., et al., *Algorithms for the diagnosis and treatment of restless legs syndrome in primary care.* BMC Neurol, 2011. 11: p. 28.
8. Garcia-Borreguero, D., et al., *Epidemiology of restless legs syndrome: the current status.* Sleep Med Rev, 2006. 10(3): p. 153-67.
9. Winkelmann, J., et al., *Genome-wide association study identifies novel restless legs syndrome susceptibility loci on 2p14 and 16q12.1.* PLoS Genet, 2011. 7(7): p. e1002171.
10. Schormair, B., et al., *PTPRD (protein tyrosine phosphatase receptor type delta) is associated with restless legs syndrome.* Nat Genet, 2008. 40(8): p. 946-8.
11. Xiang, L., et al., *Molecular genetic studies of DMT1 on 12q in French-Canadian restless legs syndrome patients and families.* Am J Med Genet B Neuropsychiatr Genet, 2007. 144B(7): p. 911-7.
12. Winkelmann, J., et al., *Genome-wide association study of restless legs syndrome identifies common variants in three genomic regions.* Nat Genet, 2007. 39(8): p. 1000-6.
13. Stefansson, H., et al., *A genetic risk factor for periodic limb movements in sleep.* N Engl J Med, 2007. 357(7): p. 639-47.
14. Stiasny-Kolster, K., et al., *Effectiveness and tolerability of rotigotine transdermal patch for the treatment of restless legs syndrome in a routine clinical practice setting in Germany.* Sleep Med, 2013. 14(6): p. 475-81.
15. Scholz, H., et al., *Levodopa for restless legs syndrome.* Cochrane Database Syst Rev, 2011(2): p. CD005504.
16. Scholz, H., et al., *Dopamine agonists for restless legs syndrome.* Cochrane Database Syst Rev, 2011(3): p. CD006009.
17. Manconi, M., et al., *Preferential D2 or preferential D3 dopamine agonists in restless legs syndrome.* Neurology, 2011. 77(2): p. 110-7.
18. England, S. J., et al., *L-Dopa improves Restless Legs Syndrome and periodic limb movements in sleep but not Attention-Deficit-Hyperactivity Disorder in a double-blind trial in children.* Sleep Med, 2011. 12(5): p. 471-7.
19. Manconi, M., et al., *First night efficacy of pramipexole in restless legs syndrome and periodic leg movements.* Sleep Med, 2007. 8(5): p. 491-7.
20. Garcia-Borreguero, D., et al., *Systematic evaluation of augmentation during treatment with ropinirole in restless legs syndrome (Willis-Ekbom disease): results from a prospective, multicenter study over 66 weeks.* Mov Disord, 2012. 27(2): p. 277-83.
21. Hogl, B., et al., *Progressive development of augmentation during long-term treatment with levodopa in restless legs syndrome: results of a prospective multi-center study.* J Neurol, 2010. 257(2): p. 230-7.
22. Garcia-Borreguero, D. and A. M. Williams, *Dopaminergic augmentation of restless legs syndrome.* Sleep Med Rev, 2010. 14(5): p. 339-46.
23. Garcia-Borreguero, D., et al., *Diagnostic standards for dopaminergic augmentation of restless legs syndrome: report from a World Association of Sleep Medicine-International Restless Legs Syndrome Study Group consensus conference at the Max Planck Institute.* Sleep Med, 2007. 8(5): p. 520-30.
24. Paulus, W. and E. D. Schomburg, *Dopamine and the spinal cord in restless legs syndrome: does spinal cord physiology reveal a basis for augmentation?* Sleep Med Rev, 2006. 10(3): p. 185-96.
25. Allen, R. P. and C. J. Earley, *Augmentation of the restless legs syndrome with carbidopa/levodopa.* Sleep, 1996. 19(3): p. 205-13.
26. Garcia-Borreguero, D., et al., *Augmentation as a treatment complication of restless legs syndrome: concept and management.* Mov Disord, 2007. 22 Suppl 18: p. S476-84.
27. Garcia-Borreguero, D., et al., *Validation of the Augmentation Severity Rating Scale (ASRS): a multicentric, prospective study with levodopa on restless legs syndrome.* Sleep Med, 2007. 8(5): p. 455-63.
28. Silver, N., et al., *A 10-year, longitudinal assessment of dopamine agonists and methadone in the treatment of restless legs syndrome.* Sleep Med, 2011. 12(5): p. 440-4.
29. Garcia-Borreguero, D., et al., *The long-term treatment of restless legs syndrome/Willis-Ekbom disease: evidence-based guidelines and clinical consensus best practice guidance: a report from the International Restless Legs Syndrome Study Group.* Sleep Med, 2013. 14(7): p. 675-84.
30. Garcia-Borreguero, D., et al., *Treatment of restless legs syndrome with pregabalin: a double-blind, placebo-controlled study.* Neurology, 2010. 74(23): p. 1897-904.
31. Allen, R., et al., *A randomized, double-blind, 6-week, dose-ranging study of pregabalin in patients with restless legs syndrome.* Sleep Med, 2010. 11(6): p. 512-9.
32. Kustermann, A., et al., *Depression and attempted suicide under pregabalin therapy.* Ann Gen Psychiatry, 2014. 13(1): p. 37.
33. Hall, T. D., et al., *Changes in mood, depression and suicidal ideation after commencing pregabalin for neuropathic pain.* Aust Fam Physician, 2014. 43(10): p. 705-8.
34. Bekhit, M. H., *Opioid-induced hyperalgesia and tolerance.* Am J Ther, 2010. 17(5): p. 498-510.

35. Winkelman, J. W., A. Gagnon, and A. G. Clair, *Sensory symptoms in restless legs syndrome: the enigma of pain.* Sleep Med, 2013. 14(10): p. 934-42.
36. Trenkwalder, C. and W. Paulus, *Restless legs syndrome: pathophysiology, clinical presentation and management.* Nat Rev Neurol, 2010. 6(6): p. 337-46.
37. Trotti, L. M. and D. B. Rye, *Restless legs syndrome.* Handb Clin Neurol, 2011. 100: p. 661-73.
38. Salas, R. E., R. Rasquinha, and C. E. Gamaldo, *All the wrong moves: a clinical review of restless legs syndrome, periodic limb movements of sleep and wake, and periodic limb movement disorder.* Clin Chest Med, 2010. 31(2): p. 383-95.
39. Winkelmann, J., *Genetics of restless legs syndrome.* Curr Neurol Neurosci Rep, 2008. 8(3): p. 211-6.
40. Picchietti, D., et al., *Restless legs syndrome: prevalence and impact in children and adolescents-the Peds REST study.* Pediatrics, 2007. 120(2): p. 253-66.
41. Trenkwalder, C., W. Paulus, and A. S. Walters, *The restless legs syndrome.* Lancet Neurol, 2005. 4(8): p. 465-75.
42. Barriere, G., et al., *The restless legs syndrome.* Prog Neurobiol, 2005. 77(3): p. 139-65.
43. Earley, C. J., et al., *Altered Brain iron homeostasis and dopaminergic function in Restless Legs Syndrome (Willis-Ekbom Disease).* Sleep Med, 2014. 15(11): p. 1288-301.
44. Earley, C. J., et al., *Increased synaptic dopamine in the putamen in restless legs syndrome.* Sleep, 2013. 36(1): p. 51-7.
45. Bayard, S., M. C. Langenier, and Y. Dauvilliers, *Decision-making, reward-seeking behaviors and dopamine agonist therapy in restless legs syndrome.* Sleep, 2013. 36(10): p. 1501-7.
46. Connor, J. R., et al., *Postmortem and imaging based analyses reveal CNS decreased myelination in restless legs syndrome.* Sleep Med, 2011. 12(6): p. 614-9.
47. Allen, R. P., et al., *Restless legs syndrome/Willis-Ekbom disease diagnostic criteria: updated International Restless Legs Syndrome Study Group (IRLSSG) consensus criteria-history, rationale, description, and significance.* Sleep Med, 2014. 15(8): p. 860-73.
48. Clemens, S., D. Rye, and S. Hochman, *Restless legs syndrome: revisiting the dopamine hypothesis from the spinal cord perspective.* Neurology, 2006. 67(1): p. 125-30.
49. Thorpe, A., et al., *Possible sites of therapeutic action in Restless Legs Syndrome: Focus on dopamine and [alpha]2[delta] ligands.* Eur Neurol, 2011. 66(1): p. 18-29.
50. Mackie, S. and J. W. Winkelman, *Long-Term Treatment of Restless Legs Syndrome (RLS):An Approach to Management of Worsening Symptoms, Loss of Efficacy, and Augmentation.* CNS Drugs, 2015. 29(5): p. 351-7.
51. Luo, F., et al., *The long-term effects of the dopamine agonist pramipexole in a proposed restless legs syndrome animal model.* Sleep Med, 2010.
52. Montplaisir, J., et al., *Restless legs syndrome improved by pramipexole: a double-blind randomized trial,* Neurology, 1999. 52(5): p. 938-43.
53. Stiasny-Kolster, K. and W. H. Oertel, *Low-dose pramipexole in the management of restless legs syndrome. An open label trial,* Neuropsychobiology, 2004. 50(1): p. 65-70.
54. Oertel, W., et al., *Long-term safety and efficacy of rotigotine transdermal patch for moderate-to-severe idiopathic restless legs syndrome: a 5-year open-label extension study,* Lancet Neurol, 2011. 10(8): p. 710-20.
55. Oertel, W. H., et al., *Rotigotine transdermal patch in moderate to severe idiopathic restless legs syndrome: a randomized, placebo-controlled polysomnographic study.* Sleep Med, 2010. 11(9): p. 848-56.
56. Davies, S., *Rotigotine for restless legs syndrome.* Drugs Today (Barc), 2009. 45(9): p. 663-8.
57. Cote, S. R. and E. V. Kuzhikandathil, *In vitro and in vivo characterization of the agonist-dependent D3 dopamine receptor tolerance property.* Neuropharmacology, 2014. 79: p. 359-67.
58. Kuzhikandathil, E. V., et al., *Identification and characterization of novel properties of the human D3 dopamine receptor.* Mol Cell Neurosci, 2004. 26(1): p. 144-55.
59. Gil-Mast, S., et al., *An amino acid residue in the second extracellular loop determines the agonist-dependent tolerance property of the human D3 dopamine receptor.* ACS Chem Neurosci, 2013. 4(6): p. 940-51.
60. Westrich, L., et al., *Development of tolerance in D3 dopamine receptor signaling is accompanied by distinct changes in receptor conformation.* Biochem Pharmacol, 2010. 79(6): p. 897-907.
61. Fiorentini, C., et al., *Reciprocal regulation of dopamine D1 and D3 receptor function and trafficking by heterodimerization.* Mol Pharmacol, 2008. 74(1): p. 59-69.
62. Surmeier, D. J., W. J. Song, and Z. Yan, *Coordinated expression of dopamine receptors in neostriatal medium spiny neurons.* J Neurosci, 1996. 16(20): p. 6579-91.
63. Missale, C., et al., *The neurobiology of dopamine receptors: evolution from the dual concept to heterodimer complexes.* J Recept Signal Transduct Res, 2010. 30(5): p. 347-54.
64. Maggio, R., et al., *Heterodimerization of dopamine receptors: new insights into functional and therapeutic significance.* Parkinsonism Relat Disord, 2009. 15 Suppl 4: p. S2-7.
65. Cruz-Trujillo, R., et al., *D3 dopamine receptors interact with dopamine D1 but not D4 receptors in the GABAergic terminals of the SNr of the rat.* Neuropharmacology, 2013. 67: p. 370-8.
66. Guitart, X., et al., *Functional Selectivity of Allosteric Interactions within G Protein-Coupled Receptor Oligomers: The Dopamine D1-D3 Receptor Heterotetramer.* Mol Pharmacol, 2014. 86(4): p. 417-29.
67. Zhu, H., et al., *Unaltered D1, D2, D4, and D5 dopamine receptor mRNA expression and distribution in the spinal cord of the D3 receptor knockout mouse.* J Comp Physiol A Neuroethol Sens Neural Behav Physiol, 2008. 194(11): p. 957-62.
68. Zhu, H., et al., *Expression and distribution of all dopamine receptor subtypes (D1-D5) in the mouse lumbar spinal cord: A real-time polymerase chain reaction and non-autoradiographic in situ hybridization study.* Neuroscience, 2007. 149: p. 885-897.
69. Clemens, S., et al., *Opposing modulatory effects of D1-and D2-like receptor activation on a spinal central pattern generator.* J Neurophysiol, 2012. 107: p. 2250-2259.
70. Dziewczapolski, G., et al., *Opposite roles of D1 and D5 dopamine receptors in locomotion revealed by selective antisense oligonucleotides.* Neuroreport, 1998. 9(1): p. 1-5.
71. Han, P. and P. J. Whelan, *Modulation of AMPA currents by D(1)-like but not D(2)-like receptors in spinal motoneurons.* Neuroscience, 2009. 158(4): p. 1699-707.
72. Han, P., et al., *Dopaminergic modulation of spinal neuronal excitability.* J Neurosci, 2007. 27(48): p. 13192-204.

73. Bubenikova-Valesova, V., et al., *The effect of a full agonist/antagonist of the D1 receptor on locomotor activity, sensorimotor gating and cognitive function in dizocilpine-treated rats.* Int J Neuropsychopharmacol, 2009. 12(7): p. 873-83.
74. Gilbert, D. L., et al., *A D1 receptor antagonist, ecopipam, for treatment of tics in Tourette syndrome.* Clin Neuropharmacol, 2014. 37(1): p. 26-30.
75. Chipkin, R. E., *Ecopipam Treatment of Tourette's Syndrome in Subjects 7-17 Years,* 2014, ClinicalTrials.gov.
76. Drago, J., et al., *Altered striatal function in a mutant mouse lacking D1A dopamine receptors.* Proc Natl Acad Sci U S A, 1994. 91(26): p. 12564-8.
77. Xu, M., et al., *Dopamine D1 receptor mutant mice are deficient in striatal expression of dynorphin and in dopamine-mediated behavioral responses.* Cell, 1994. 79(4): p. 729-42.
78. Darmopil, S., et al., *Genetic inactivation of dopamine D1 but not D2 receptors inhibits L-DOPA-induced dyskinesia and histone activation.* Biol Psychiatry, 2009. 66(6): p. 603-13.
79. Xu, M., et al., *Elimination of cocaine-induced hyperactivity and dopamine-mediated neurophysiological effects in dopamine D1 receptor mutant mice.* Cell, 1994. 79(6): p. 945-55.
80. Keeler, B. E., et al., *Increased excitability of spinal pain reflexes and altered frequency-dependent modulation in the dopamine D3-receptor knockout mouse.* Exp Neurol, 2012. 238(2): p. 273-283.
81. Brewer, K. L., et al., *Dopamine D3 receptor dysfunction prevents anti-nociceptive effects of morphine in the spinal cord.* Frontiers in Neural Circuits, 2014. 8: p. 62-01 62-10.
82. Baier, P. C. and C. Trenkwalder, *Circadian variation in restless legs syndrome.* Sleep Med, 2007. 8(6): p. 645-50.
83. Granado, N., S. Ares-Santos, and R. Moratalla, *D1 but not D4 dopamine receptors are critical for MDMA-induced neurotoxicity in mice.* Neurotox Res, 2014. 25(1): p. 100-9.
84. Breese, N. M., et al., *Peripheral inflammation selectively increases TRPV1 function in I84-positive sensory neurons from adult mouse.* Pain, 2005. 115(1-2): p. 37-49.
85. Djouhri, L., et al., *Spontaneous pain, both neuropathic and inflammatory, is related to frequency of spontaneous firing in intact C-fiber nociceptors.* J Neurosci, 2006. 26(4): p. 1281-92.
86. Wei, L., *Immunological aspect of cardiac remodeling: T lymphocyte subsets in inflammation-mediated cardiac fibrosis.* Exp Mol Pathol, 2011. 90(1): p. 74-8.
87. Huang, X. R., et al., *Smad3 mediates cardiac inflammation and fibrosis in angiotensin II-induced hypertensive cardiac remodeling.* Hypertension, 2010. 55(5): p. 1165-71.
88. Johnson, T. L., et al., *The dopamine D3 receptor knockout mouse mimics aging-related changes in autonomic function and cardiac fibrosis.* PLoS One, 2013. 8(8): p. e74116.
89. Hubble, J. P., *Pre-clinical studies of pramipexole: clinical relevance.* Eur J Neurol, 2000. 7 Suppl 1: p. 15-20.
90. Rascol, O., *Dopamine agonists: what is the place of the newer compounds in the treatment of Parkinson's disease?* J Neural Transm Suppl, 1999. 55: p. 33-45.
91. Kuzhikandathil, E. V. and G. S. Oxford, *Activation of human D3 dopamine receptor inhibits P/Q-type calcium channels and secretory activity in AtT-20 cells.* J Neurosci, 1999. 19(5): p. 1698-707.
92. Clemens, S. and S. Hochman, *Conversion of the modulatory actions of dopamine on spinal reflexes from depression to facilitation in D3 receptor knock-out mice.* J Neurosci, 2004. 24(50): p. 11337-45.
93. Dougherty, K. J., M. A. Sawchuk, and S. Hochman, *Properties of mouse spinal lamina I GABAergic interneurons.* J Neurophysiol, 2005. 94(5): p. 3221-7.
94. Machacek, D. W., et al., *Serotonin 5-HT(2) receptor activation induces a long-lasting amplification of spinal reflex actions in the rat.* J Physiol, 2001. 537(Pt 1): p. 201-7.
95. Shreckengost, J., et al., *Bicuculline-sensitive primary afferent depolarization remains after greatly restricting synaptic transmission in the mammalian spinal cord.* J Neurosci, 2010. 30(15): p. 5283-8.
96. Malik, P., M. B. Andersen, and L. Peacock, *The effects of dopamine D3 agonists and antagonists in a nonhuman primate model of tardive dyskinesia.* Pharmacol Biochem Behav, 2004. 78(4): p. 805-10.
97. Pham, A. N. and T. D. Waite, *Cu(II)-catalyzed oxidation of dopamine in aqueous solutions: mechanism and kinetics.* J Inorg Biochem, 2014. 137: p. 74-84.
98. Massad, W. A., et al., *Vitamin B-sensitized photooxidation of dopamine.* Photochem Photobiol, 2008. 84(5): p. 1201-8.
99. Iuga, C., J. R. Alvarez-Idaboy, and A. Vivier-Bunge, *ROS initiated oxidation of dopamine under oxidative stress conditions in aqueous and lipidic environments.* J Phys Chem B, 2011. 115(42): p. 12234-46.
100. DeAndrade, M. P., et al., *Motor restlessness, sleep disturbances, thermal sensory alterations and elevated serum iron levels in Btbd9 mutant mice.* Hum Mol Genet, 2012. 21(18): p. 3984-92.
101. Schormair, B., et al., *MEIS1 and BTBD9: genetic association with restless leg syndrome in end stage renal disease.* J Med Genet, 2011. 48(7): p. 462-6.
102. Spieler, D., et al., *Restless legs syndrome-associated intronic common variant in Meis1 alters enhancer function in the developing telencephalon.* Genome Res, 2014. 24(4): p. 592-603.

That which is claimed:

1. A method of treating augmentation associated with restless legs syndrome (RLS) treatment in a subject in need thereof, comprising administering to the subject an effective amount of ecopipam, thereby treating augmentation in the subject.

2. The method of claim 1, wherein the ecopipam is administered in combination with a $D_3$ receptor agonist.

3. The method of claim 1, wherein the method delays the daily onset of RLS symptoms in the subject relative to treatment with a $D_3$ receptor agonist alone.

4. The method of claim 1, wherein the method increases the latency to onset of RLS symptoms in the subject when at rest relative to treatment with a $D_3$ receptor agonist alone.

5. The method of claim 1, wherein the method reduces the intensity of symptoms in the subject relative to treatment with a $D_3$ receptor agonist alone.

6. The method of claim 1, wherein the method reduces expansion of symptoms to upper limbs and trunk of the subject relative to treatment with a $D_3$ receptor agonist alone.

7. The method of claim 2, wherein the $D_3$ receptor agonist is nafadotride, PD 128907, pramipexole, pergolide, rotigotine, or mixtures thereof.

8. The method of claim 7, wherein the $D_3$ receptor agonist is pramipexole.

9. A method of restoring responsiveness or decreasing tolerance to a $D_3$ receptor agonist in a subject in need thereof, comprising activating a $D_3$ receptor pathway and inhibiting $D_1$ receptor activity by administering ecopipam to the subject after $D_3$ receptor-mediated reduction in responsiveness or increased tolerance to a $D_3$ receptor agonist in the subject, thereby restoring responsiveness or decreasing tolerance to the $D_3$ receptor agonist.

10. The method of claim 9, wherein the subject is at risk for or suffers from augmentation.

11. The method of claim 9, wherein the $D_3$ receptor agonist is nafadotride, PD 128907, pramipexole, pergolide, rotigotine, or mixtures thereof.

12. The method of claim 11, wherein the $D_3$ receptor agonist is pramipexole.

* * * * *

UNITED STATES PATENT AND TRADEMARK OFFICE
CERTIFICATE OF CORRECTION

| | | |
|---|---|---|
| PATENT NO. | : 12,220,404 B2 | Page 1 of 1 |
| APPLICATION NO. | : 16/932352 | |
| DATED | : February 11, 2025 | |
| INVENTOR(S) | : Clemens et al. | |

It is certified that error appears in the above-identified patent and that said Letters Patent is hereby corrected as shown below:

In the Specification

Column 15, Line 42: Please correct "a set" to read --α set--

Column 15, Line 65: Please correct "D1K0" to read --D1KO--

Column 17, Line 54: Please correct "a set" to read --α set--

Column 24, Line 38: Please correct "*Meisl*" to read --*Meis1*--

Signed and Sealed this
Fifteenth Day of July, 2025

Coke Morgan Stewart
*Acting Director of the United States Patent and Trademark Office*